United States Patent [19]

Chada et al.

[11] Patent Number: 5,736,388

[45] Date of Patent: Apr. 7, 1998

[54] BACTERIOPHAGE-MEDIATED GENE TRANSFER SYSTEMS CAPABLE OF TRANSFECTING EUKARYOTIC CELLS

[76] Inventors: Sunil Chada, 1542 Enchantment Ave., Vista, Calif. 92083; Thomas W. Dubensky, Jr., 12729 via Felino, Del Mar, Calif. 92014

[21] Appl. No.: 366,522

[22] Filed: Dec. 30, 1994

[51] Int. Cl.$^6$ .......................... C12N 15/85; C12N 15/88; A61K 48/00
[52] U.S. Cl. .................. 435/320.1; 424/93.6; 435/172.3; 435/235.1; 514/44
[58] Field of Search .................. 435/320.1, 172.3, 435/240.1, 235.1; 514/2, 44; 424/93.21

[56] References Cited

FOREIGN PATENT DOCUMENTS

WO 94/17832  8/1994  WIPO.

OTHER PUBLICATIONS

Graham et al., Virology (1973) 52:456–461.
Marshall, Science 269:1050–1055, 1995.
Miller et al., FASEB J. 9:190–199, 1995.
Culver et al., Trends in Genetics 10(5):174–178, 1994.
Hodgson, Exp. Opin. Ther. Pat. 5(5):459–468, 1995.
Werts et al., J. Bacteriol. 176:941–947, 1994.
Francis et al., Appl. Environ. Microbiol 59(9):3060–3055, 1993.
Becker et al., Proc. Natl. Acad. Sci., 72:581–585, 1975.
Horst et al., Proc. Natl. Acad. Sci. US 72:3531–3535, 1975.
Ishiura et al., Mol. Col. Biol. 2:607–616, 1982.
Okayama et al., Mol. Cell. Biol. 5:1136–1142, 1985.
Shibata et al., Biochemie, France 75:459–465, 1993.
Srivatsan et al., Cytogenet. Cell. Genet. 38:227–234, 1984.
Werts et al., J. Bacteriol., 176:941–947, 1994.
Hert et al., J. Biol. Chem., 269(17):12468–12474, 1994.
Maruyama et al., Proc. Natl. Acad. Sci., 91:8273–8277, 1994.

Primary Examiner—Jasemine C. Chambers
Assistant Examiner—Scott D. Priebe
Attorney, Agent, or Firm—Norman J. Kruse; Robert P. Blackburn

[57] ABSTRACT

Lamboid bacteriophage capable of specifically interacting with and delivering nucleic acid molecules to eukaryotic cells are disclosed. Such bacteriophage-derived gene transfer systems target one or more specific receptors on eukaryotic cells, for instance by incorporating mutant tail fiber proteins or by incorporating known ligands for specific eukaryotic receptors into lambda phage. Also disclosed are methods for identifying and producing modified bacteriophage tail fiber polypeptides capable of specifically interacting with eukaryotic transmembrane proteins. Methods of treating diseases using such gene transfer systems are also disclosed.

4 Claims, 2 Drawing Sheets

BACTERIOPHAGE-MEDIATED GENE TRANSFER SYSTEMS CAPABLE OF TRANSFECTING EUKARYOTIC CELLS

FIELD OF THE INVENTION

This invention relates to gene transfer systems useful for the delivery of nucleic acid molecules encoding nucleic acid sequences to cells. In particular, this invention relates to bacteriophage-mediated gene transfer systems capable of delivering specific nucleic acid molecules to animal cells.

BACKGROUND OF THE INVENTION

Since the discovery of DNA and continuing through to the recent era of genetic engineering, substantial research has been undertaken in order to realize the possibility that the course of disease may be affected through interaction with the nucleic acids of living organisms. Most recently, a wide variety of compositions and methods have been described for the delivery to an animal of heterologous genes, i.e., those not normally found in the animal. These efforts, refered to as "gene therapy." The goal has been to develop more effective treatments for disease, particularly those which, at present, are untreatable or are treated with only a modicum of success.

Present gene therapy regimens typically employ viral vectors derived from retroviruses, adenoviruses, vaccinia viruses, herpes viruses, and adeno-associated viruses (see Jolly, *Cancer Gene Therapy* 1(1):51–64, 1994), as well as direct transfer techniques such as lipofection (Felgner et al., *Proc. Natl. Acad. Sci. USA* 84:7413–7417, 1989), direct DNA injection (Acsadi et al., *Nature* 352:815–818, 1991), microprojectile bombardment (Williams et al., *PNAS* 88:2726 . 2730, 1991), liposomes of several types (see, e.g., Wang et al., *PNAS* 84:7851–7855, 1987) and administration of nucleic acids alone (WO 90/11092).

Of these techniques, recombinant retroviral gene transfer systems have been most extensively utilized. In particular, retroviruses are diploid positive-strand RNA viruses that replicate in eukaryotic cells through an integrated DNA intermediate. Briefly, upon infection by the RNA virus, the retroviral genome is reverse-transcribed into DNA by a virally encoded reverse transcriptase that is carried as a protein in each retroviral particle. The viral DNA is then integrated into the genome of the infected cell, forming a "provirus" which is inherited by daughter cells.

Wild-type retroviral genomes from numerous retroviruses have been characterized and several have been manipulated through application of recombinant DNA techniques to generate vectors useful for the insertion of heterologous genes into eukaryotic cells. These retroviral vectors and various uses thereof have been described in numerous references including, for example, Mann et al. (*Cell* 33:153, 1983), Cane and Mulligan (*Proc. Nat'l. Acad. Sci. USA* 81:6349, 1984), Miller et al., *Human Gene Therapy* 1:5–14, 1990, U.S. Pat. Nos. 4,405,712; 4,861,719; 4,980,289 and PCT Application Nos. WO 89/02,468; WO 89/05,349 and WO 90/02,806. Briefly, a foreign gene of interest (the heterologous gene) may be incorporated into the retrovirus in place of a portion of the normal retroviral genome. Upon delivery into a cell, the foreign gene is also introduced into the cell, and may then be integrated into the host's cellular DNA as if it were the retrovirus itself. Expression of this foreign gene within the host results in expression of a heterologous molecule, e.g., a polypeptide, antisense RNA, or ribozyme encoded thereby, in the host cell.

One disadvantage, however, of recombinant retroviruses is that they principally infect only replicating cells, thereby making efficient direct gene transfer difficult. Alternatively, it has been suggested that other, more efficient methods of gene transfer, such as direct administration of pure plasmid DNA, be utilized (Davis et al., *Human Gene Therapy* 4:733–740, 1993). Furthermore, due to the manner in which recombinant retroviruses are typically prepared, they may be quickly inactivated by components in the blood of a patient to whom the retrovirus is administered.

Other recombinant vital gene transfer systems have also been developed, such as adenovirus and pox virus systems. However, such systems also suffer from disadvantages, such as pre-existing immunity in patients to be treated therewith and large, relatively uncharacterized genomes.

As a result of these and other deficiencies of current gene transfer systems, a need exists for the development of yet other systems to exploit the potential of gene therapy approaches to disease treatment.

Bacteriophages are a diverse group of viruses that replicate in bacterial cells. One of the most studied of these viruses is bacteriophage lambda ("lambda") which replicates in *E. coli*. Lambda has a number of advantages over related phage which have lead to it being one of the most intensively studied genetic elements. The lysogenic form of lambda was first discovered in 1921, although the concept of lysogeny remained controversial for many years. It took another 30 years for induction of prophage to be amply demonstrated. Many fundamental discoveries relating to various scientific disciplines are rooted in basic lambda biology. Such discoveries include: hereditary transmission of a virus, recombination mechanisms, congruency between genetic linkage maps and the DNA molecule, DNA replication mechanisms, molecular cloning methodology, and genetic repressor elements in gene regulation. Many of these basic discoveries in bacterial research have had direct correlates in eukaryotic and, often, in mammalian molecular biology.

In a limited number of experiments, lambda phage have been used as a delivery vehicle to non-specifically mediate gene transfer into eukaryotic cells by direct incubation with cultured cells (Srivatsan 1984, Okayama 1985, Horst 1975, and Ishiura 1982). These experiments took advantage of the protection against nucleolytic action by encapsidated phage; however, the bacteriophage mediated gene transfer efficiency was very low.

The inherent properties of lambda have made it an extremely successful gene transfer agent in bacteria. Inventive application of recombinant DNA techniques enables generation of bacteriophage which have the ability to infect eukaryotic cells, including human cells, in a specific and controlled manner. The use of bacteriophage as gene transfer systems for direct DNA transfer in vivo has at least three major advantages over direct, or "naked," DNA injection techniques:

1. High Production Capacity

Bacteriophage are produced from bacteria in high yield, often at levels 10–100 times greater than the yield of plasmid DNA obtained from transformed bacteria. For instance, levels of lambda phage that can be obtained from a lysed bacterial culture can exceed $10^{11}$ pfu/ml (Blattner et al., 1977), and a one liter shake flask culture can provide $10^{14}$ phage, whereas a similar one liter culture will provide 500–5000 mg of plasmid DNA. Optimization of bacteriophage growth conditions in high density bacterial culture can provide a further increase in yield of 10- to 100-fold.

Beyond production of high levels of phage per unit volume, bacteriophage can also carry large nucleic acid inserts. If the packaging components are supplied in trans, as in in vitro production of lambda, nucleic acid molecules of up to and sometimes greater than 50 kb can be efficiently packaged (Hendrix et al., 1983). A 100 kb capacity for heterologous genetic material, using the generalized transducing bacteriophage P1, has been recently described (Sternberg, N. *PNAS* 87:103–107).

2. Stability of Bacteriophage Particles

Bacteriophage are routinely purified in research laboratories using techniques such as chloroform treatment of bacteria lysates, differential or equilibrium sedimentation or polyethylene glycol precipitation (Hendrix et al., 1983). Phage are resistant to treatment with DNase and RNase. This resistance to certain organic chemicals, harsh purification procedures, and exogenous nucleases provides an important benefit to the use of phage as gene transfer systems. Yield of infectious phage after a number of purification steps is often over 30% compared to the initial titer. In addition, nucleic acids carried by phage DNA are complexed within capsids in a condensed, "protected" form, as discussed in more detail below. An important component for phage stability is the presence of $Mg^{+2}$.

3. Ease of Manufacture

Bacteriophage are also easy to produce in large quantities and in high titers, which are important considerations in the design and use of gene transfer systems. Phage can be grown in liquid culture as lytic agents which lyse their host bacteria or, alternatively, as lysogens which can be grown to high density and then induced in a batch method. Phage and their host bacteria are stable, easy and inexpensive to propagate. Bacteria can be grown to very high densities and are routinely infected with lambda at densities of $3 \times 10^8$ bacteria/mL. High titer products can be produced very rapidly. The life cycle of lambda is complete in less than one hour and about 100 progeny phage are released per bacterial host cell.

Bacteriophage can also be produced in vitro by mixing a purified nucleic acid molecule with head and tail components available from bacterial lysates. The phage specified nucleic acid packaging proteins are readily available and require only input nucleic acid molecules and ATP for self-assembly of intact virions. Although the efficiency of packaging only approximates 10%, phages, once packaged, are functional and form plaques on *E. coli* with an efficiency of 100%. The current generation of in vitro packaging systems are efficient and can yield up to $2 \times 10^9$ pfu (plaque forming units) per microgram of input DNA (Kretz et al., 1989).

These and other aspects and embodiments of the invention will become evident upon reference to the following detailed description and attached figures.

SUMMARY OF THE INVENTION

It is the object of this invention to construct new gene transfer systems based on bacteriophage-mediated gene delivery that can specifically interact with eukaryotic cells and deliver nucleic acid molecules to those cells.

Within one aspect of the present invention, a bacteriophage particle is provided capable of specifically interacting with an animal cell and delivering into the animal cell a nucleic acid molecule. In one embodiment, the bacteriophage particle comprises a modified tail fiber polypeptide that interacts specifically with a transmembrane protein of a cell membrane of the cell. The bacteriophage particle may be derived from a bacteriophage lambda particle, wherein the modified tail fiber polypeptide is a modified gpJ polypeptide. In another embodiment, the nucleic acid molecule encodes an heterologous nucleic acid molecule. The heterologous nucleic acid molecule codes for a compound selected from the group consisting of a polypeptide, an anti-sense RNA, and a ribozyme.

Within another aspect of the invention, a method is provided for producing a modified bacteriophage tail fiber polypeptide capable of specifically interacting with a transmembrane protein of a cell membrane of an animal cell. The method comprising cultivating, under appropriate nutrient conditions, a eukaryotic or prokaryotic host microorganism harboring a nucleic acid molecule. In one embodiment, the modified bacteriophage particle carries a nucleic acid molecule encoding an exogenous nucleic acid sequence. The method comprising combining, in vitro, a head extract comprising the nucleic acid molecule in a prohead and tail extract comprising a modified bacteriophage tail fiber polypeptide capable of specifically interacting with a transmembrane protein of a cell membrane of an animal. Within the various aspects of the invention, a method is provided for treating a diseased animal comprising administering to the animal a therapeutically effective amount of this gene transfer system. The method of treatment being vaccinating an animal comprising administering to the animal an immunologically effective amount of a gene transfer system. The diseased animal having a disease selected from the group consisting of cancer, an autoimmune disease, an infection, a genetic disease, and a graft versus host disease. The preferred diseased animal is human.

Within still another aspect of the invention a method is provided for identification of a modified bacteriophage tail fiber polypeptide capable of specifically interacting with a transmembrane protein of an animal cell. The method comprising mutagenizing a nucleic acid molecule coding for a bacteriophage tail fiber protein so that the nucleic acid molecule codes for one or more bacteriophage tail fiber protein analogues, expressing the bacteriophage tail fiber protein analogues, screening the bacteriophage tail fiber protein analogues for an ability to specifically interact with a transmembrane protein of an animal, and identifying the bacteriophage tail fiber protein analogues (or mutants) that specifically interact with a transmembrane protein of an animal cell.

In various aspects of the invention the bacteriophage-mediated gene transfer system containing the nucleic acid molecules, the nucleic acid molecule encoding the modified bacteriophage lambda gpJ protein, the vector construct comprising the nucleic acid molecule, and the eukaryotic or prokaryotic host harboring the vector construct is provided.

DEFINITIONS

Figure 1A:
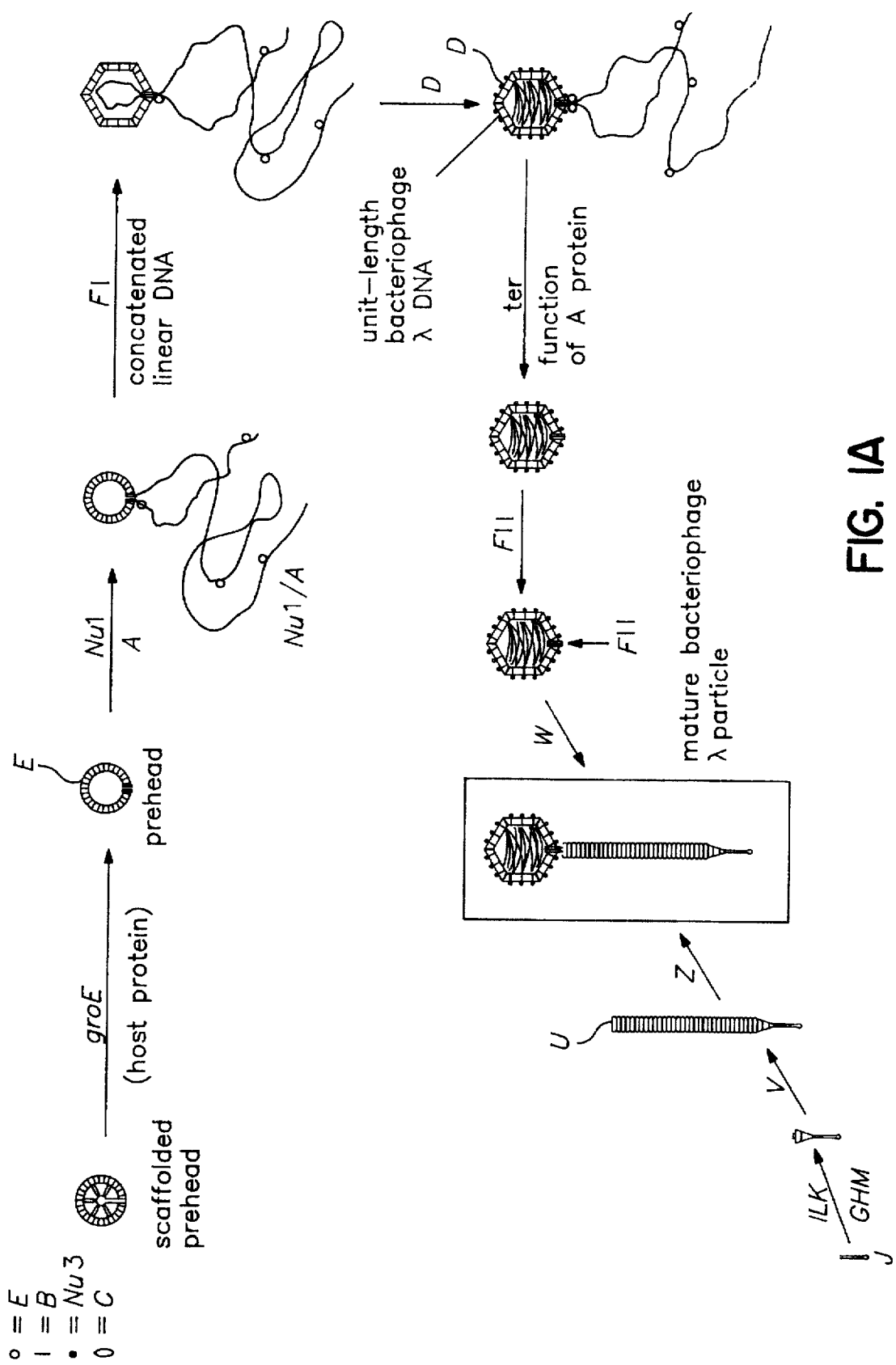
FIG. 1 (A) is a diagrammatic representation of the bacteriophage lambda assembly pathway. (B) is a diagrammatic representation of an intact bacteriophage lambda particle including a cross section of the tail region.

The following terms are used throughout the specification. Unless otherwise indicated, these terms are defined as follows:

A "bacteriophage structural protein" refers to a polypeptide which comprises a part of the physical structure of an infectious bacteriophage particle. Such proteins include those comprising the head, capsid, and tail structures.

"Vector", "vector construct", "recombinant vector", and "recombinant vector construct" refer to a nucleic acid molecule capable of directing the expression of one or more genes of interest encoded thereon. Such vectors will also include bacteriophage packaging signals, and at least one promoter to direct the expression of the gene(s) of interest. Various other types of regulatory sequences, as discussed below, may also be included on such vectors.

A "gene transfer system" refers to a construct which is capable of delivering, and, within preferred embodiments expressing, one or more gene(s) or sequence(s) of interest in a host cell. Representative examples of such vehicles include viral vectors, nucleic acid expression vectors, naked DNA, and a bacteriophage capable of specifically interacting with a eukaryotic cell and delivering into the cell a nucleic acid molecule.

A "targeting element" refers to a molecule which is capable of specifically binding a selected cell type. As utilized within the context of the present invention, targeting elements are considered to specifically bind a selected cell type when a biological effect of the coupled targeting element may be seen in that cell type, or, when there is greater than a 10 fold difference, and preferably greater than a 25, 50 or 100 fold difference between the binding of the coupled targeting element to target cells and non-target cells. Generally, it is preferable that the targeting element bind to the selected cell type with a $K_D$ of less than $10^{-5}M$, preferably less than $10^{-6}M$, more preferably less than $10^{-7}M$, and most preferably less than $10^{-8}M$ (as determined by a Scatchard analysis, see Scatchard, *Ann. N.Y. Acad. Sci.* 51:660–672, 1949). Suitable targeting elements are preferably non-immunogenic, not degraded by proteolysis, and not scavenged by the immune system. Particularly preferred targeting elements (which are conjugated to a member of the high affinity binding pair) should have a half-life (in the absence of a clearing agent) within an animal of between 10 minutes and 1 week. Representative examples of suitable targeting elements are set forth below in more detail.

A "high affinity binding pair" refers to a set a molecules which is capable of binding one another with a $K_D$ of less than $10^{-y}M$, wherein y is selected from the group consisting of 8, 9, 10, 11, 12, 13, 14 and 15. As utilized herein, the "$K^D$" refers to the disassociation constant of the reaction $A+B \leftrightarrows AB$, wherein A and B are members of the high affinity binding pair. (In addition, as should be understood by one of ordinary skill in the art, as the affinity of the two molecules increases, $K_D$ decreases.) Affinity constants may be readily determined by a variety of techniques, including for example by a Scatchard analysis (see Scatchard, *Ann. N.Y. Acad. Sci.* 51:660–672, 1949). Representative examples of suitable affinity binding pairs include biotin/avidin, cytostatin/papain, phosphonate/carboxypeptidase A, and 4CABP/RuBisCo.

A "nucleic acid expression vector" refers to an assembly which is capable of directing the expression of a sequence or gene of interest. The nucleic acid expression vector must include a promoter which, when transcribed, is operably linked to the sequence(s) or gene(s) of interest, as well as a polyadenylation sequence. Within certain embodiments of the invention, the nucleic acid expression vectors described herein may be contained within a plasmid construct. In addition to the components of the nucleic acid expression vector, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

A "vector construct" refers to an assembly which is capable of directing the expression of the sequence(s) or gene(s) of interest. The vector construct will typically include transcriptional promoter/enhancer or locus defining element(s), or other elements which control gene expression by other means such as alternate splicing, nuclear RNA export, post-translational modification of messenger, or post-transcriptional modification of protein. In addition, the vector construct will typicalIly include a sequence which, when transcribed, is operably linked to the sequence(s) or gene(s) of interest and acts as a translation initiation sequence. Optionally, the vector construct may also include a signal which directs polyadenylation, a selectable marker such as a gene conferring resistance to an antibiotic such as neomycin, hygromycin, phleomycin, histidinol, or methotrexate, as well as one or more restriction sites and a translation termination sequence. In addition, if the vector construct is placed into a bacteriophage such as lambda, the vector construct must include a packaging signal such as a cos site.

An "altered cell" refers to a cell which is responsible for or involved in a disease state. Representative examples of altered cells include tumor cells, autoreactive immune cells, cells over-expressing one or more hormones, cells which lack an otherwise normal function, cells that inappropriately express one or more genes not normally expressed in that cell type, and cells infected with bacteria, viruses, or other intracellular parasites. In addition, an "altered cell" may refer to a cell which has become tumorigenic due to inappropriate insertion its genome.

A "pathogenic agent" refers to a bacteria, virus, or other pathogen capable of infecting, transducing, or otherwise altering a eukaryotic cell.

A "tissue-specific promoter" refers to a transcriptional promoter/enhancer, locus defining element, or other element involved in preferential transcriptional regulation of gene expression in a limited number of tissue types.

An "event-specific promoter" refers to a transcriptional promoter/enhancer, locus defining element, or other element which regulates gene expression in response to cellular stimuli. Representative examples of such event-specific promoters include thymidine kinase or thymidilate synthase promoters, a or b interferon promoters and promoters that respond to the presence of hormones (either natural, synthetic, or from other non-host organisms, e.g., insect hormones). Also included as "event-specific promoters" are those regulatory elements present in a eukaryotic cell as a result of infection or transduction.

Numerous aspects and advantages of the invention will be apparent to those skilled in the art upon consideration of the following detailed description which provide illumination of the practice of the invention.

DETAILED DESCRIPTION

The present invention relates to new gene transfer systems, namely bacteriophage-mediated gene transfer systems that can specifically interact with eukaryotic cells and deliver nucleic acid molecules thereto. Such vehicles are based on the ability to modify one or more of the structural proteins of various bacteriophages.

The bacteriophage-mediated gene transfer systems described herein provide for the specific delivery of therapeutic nucleic acid molecules to eukaryotic cells. The vectors incorporated into such systems may be engineered to contain a wide variety of therapeutic genes under the control of various promoters and other regulatory elements, as described below. In addition, vectors according to the invention may be modified to eliminate most or nearly all bacteriophage sequences, thereby greatly increasing therapeutic gene(s) packaging capability. In one embodiment, the only lambda nucleotide sequences contained in the vector are the two cos sites (12 bp each) are the the 5' and 3' ends of a linear fragment to be packaged in a lambda particle, leaving up to about 50 kb availible for therapeutic gene or other sequences. These and other cosmid versions of the gene transfer system require the use of specific mutant gpJ-containing in vitro packaging extracts to generate infectious bacteriophage particles. Cosmids are nucleic acid molecules which carry cos sequences necessary for bacteriophage packaging. Also included is an origin of replication (usually ColE1) which allows replication in bacteria, and frequently a gene coding for a selctable marker. Heterologous nucleic acid molecules are cloned into the cosmid vector between the cos sites.

Overview of Lambda Phage Biology

The biology of lambda-derived vectors is extremely well understood. Lambda is a temperate phage, i.e., it can grow in either a lyric or lysogenic fashion. When lambda infects a host bacterium, it injects its DNA into the host. During lytic growth, many copies of the genome are replicated and packaged into progeny phage particles which are released after lysis of the host. The life cycle of lambda is completed in less than one hour with the release of about 100 progeny phage particles per bacterial host cell. In lysogenic growth, lambda DNA is integrated into the host chromosome where it is replicated along with the host DNA. If the host cell is damaged or otherwise activated, the lambda DNA is excised from the host chromosome and the phage begins to grow lyrically. The lambda genome is grouped into discrete blocks of functionally related genes. Phage-based cloning vectors have deletions in large stretches of DNA which are not required for lytic growth; in some vectors more than 20 kb of foreign DNA can be incorporated.

Figure 1B:
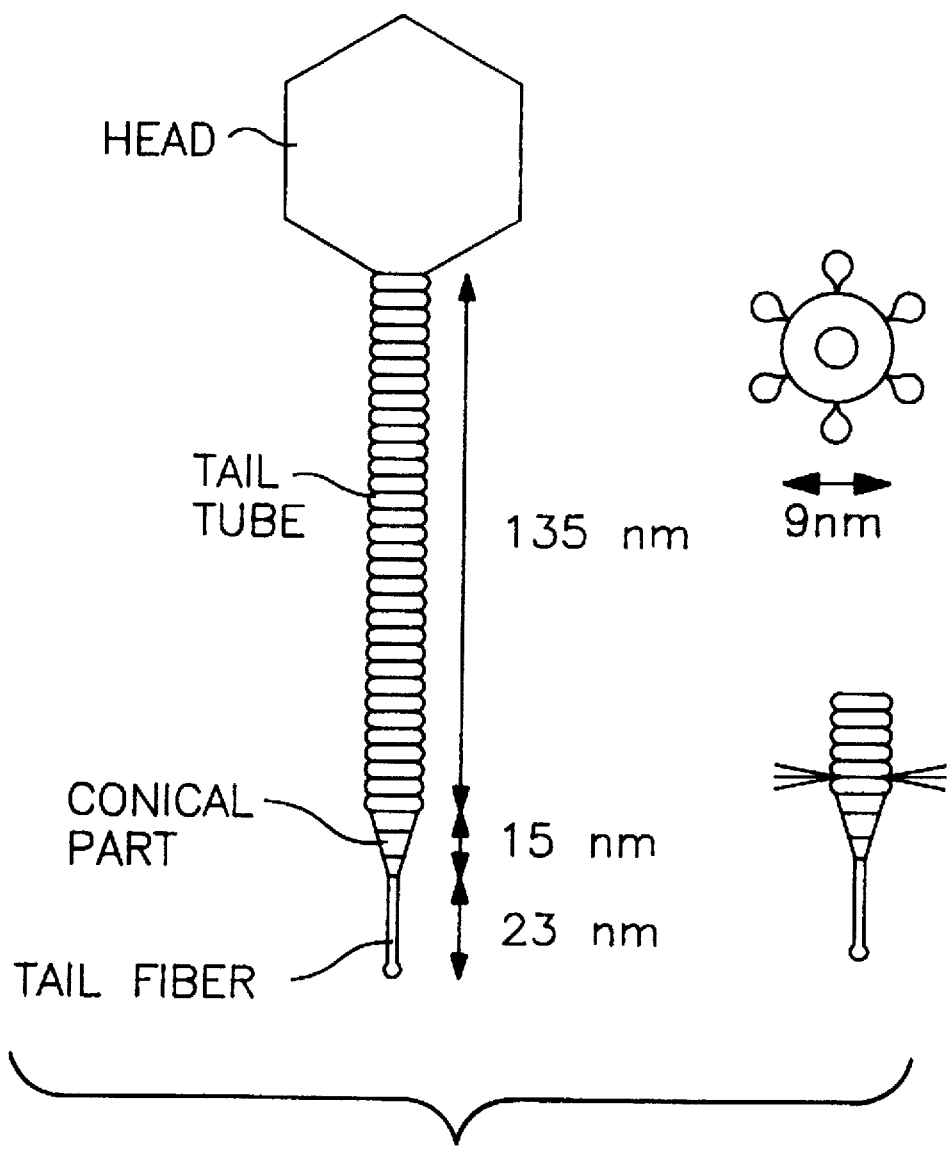

Lambda phage is composed of a capsid/head structure containing the DNA genome, a tail structure of 135 nm composed of 32 disks of gpV protein and a terminal fiber structure of 23 nm composed of the gpJ protein (see FIG. 1). It is known that lambda head and tail structures can be assembled independently and joined at the final stage of phage maturation (Weigle, 1966, 1968,Harrison et al., 1973). DNA in a phage capsid is tightly condensed (Bazinet and King, 1985). The capsid shells are assembled empty and then the DNA is threaded into the prohead shells in a complex, regulated process.

Lambda can package linear DNA molecules ranging in size from about 38 kb to about 53 kb (about 78% to about 105% of the wild type lambda genome size), although packaging efficiency declines when less than about 45 kb are packaged.

Late in lambda infection, DNA replication and packaging occur concurrently. Rolling circle DNA replication produces concatamers of full length phage genomes. The 12 bp cohesive ends at each end of the lambda genome (cos sites) are recognized by lambda proteins and the DNA between two cos sites is cleaved from the concatamer coincident with its packaging into a single prohead. The cleavage product is a linear DNA molecule of unit genome size with complementary single-stranded cohesive ends. The remaining head proteins then assemble and the tail, which has been assembled independently, attaches to the head to form an intact infectious phage (see FIG. 1).

Twelve genes are involved in tail assembly: Z, U, V, G, T, H, 208, M, L, K, I and J. These genes are arranged in a linear order on the left end of the lambda chromosome and comprise about 13 kb of the 52 kb wild type genome. Tail assembly starts with gpJ to form the initiator complex composed of J, I, L, K, H, G, M proteins. Formation of the initiator complex allows polymerization of gpV, the major tail protein. The addition of gpU and gpZ provide termination and maturation functions and generate a mature tail which can bind head structures (Hendrix et al., 1983).

The final step in assembly of functional phage from mixtures of heads and tails is a rapid process of self assembly which requires only ATP as an energy source.

Lambda parasitizes the sugar transport mechanism of bacteria to inject its DNA into the host. Lambda phage binds to its bacterial receptor (the lamB protein, the maltose receptor or porin) via the fiber structure at the end of the tail (Thirion and Hofnung, 1972). The tail fiber is composed of one protein subunit, the gpJ protein, which self-assembles in packaging bacteria or in vitro. Conditions have been determined in vitro whereby purified *E. coli* lamB receptor extracts can be mixed with lambda phage leading to spontaneous ejection of encapsidated DNA through the porin of the lamB gene product. Treatment with ethanol or chloroform can allow irreversible binding of phage to bacteria and subsequent phage DNA ejection. The absence of organic solvent treatments leads to binding but not DNA ejection with the lamB receptor of *E. coli* K 12 receptor. Mutations in gpJ of lambda or the host receptor can overcome the ethanol or chloroform treatments. Lambda mutants known as extended host range mutants, h and hh*, map to the terminal 10% of the gpJ gene and alter amino-acid residues located near the carboxyl end of gpJ (Shaw et al, 1977). h and hh* mutants spontaneously eject their DNA in vitro when exposed to lamB protein.

In *E. coli*, the pts M and pts P proteins found in the inner membrane also appear to play an essential role in lambda DNA injection. These proteins are components of the phosphoenolpyruvate-dependent phosphotransferase system for transport and phosphorylation of mannose and other sugars. However, lambda mutations which overcome these host mutations cluster in gpJ, gpH and gpV. The gpH and gpV genes play a role in initiation of DNA ejection.

In *E. coli*, adsorption of phage to the host cell requires only an interaction between the tail fiber structure and the lamB receptor. In *E. coli* K12, DNA injection requires the function of the pts M and pts P proteins as described above; however, this requirement can be overcome by the appropriate mutations in the phage. With isolated receptor proteins, DNA ejection from intact phage is facilitated by treatment with organic solvents when *E. coli* lamB protein is used as the porin. Mutations in gpJ can overcome the requirement for the organic solvents in DNA ejection. In *E. coli* K12, there are two types of lambda-host receptor complexes. Type I complex involves adsorption and binding of lambda gpJ to host lamB receptors. Type II complexes involve an interaction between the lambda tail fiber and the pts P and pts M proteins found in the inner membrane. DNA ejection appears to follow formation of the type II complex.

It is also known that the lamB protein from *Shigella sonnei* 3070 does not require organic solvent treatment to be a functional substrate for DNA ejection. In addition, Shigella infection by lambda is not dependent on the pts M or pts P proteins (Roessner and Ihler, 1987). The interaction of lambda with Shigella leads rapidly to the formation of a type II complex and DNA ejection. The sequence of *E. coli* and Shigella lamB genes have been compared and demonstrate significant similarity. Only one region of variability between the two receptors was found between residues 381–390, in which seven of the ten amino acids are different. This region is involved in the spontaneous triggering and DNA ejection from lambda (Roessner and Ihler, 1987).

Without being bound to a particular theory, this information reflects the "poised" state of the DNA injection machinery in lambda phage. The gpH protein is proteolytically cleaved after gpV polymerization and it is believed that this high energy cleavage product provides the energy for protein reorganization during DNA ejection. Binding of the lambda tail fiber to lamB causes a conformational change in the tail structure. In *E. coli*, a second event involving the pts M and pts P proteins provides the activating signal for protein reorganization and DNA ejection. However, Shigella lamB receptor provides both binding and secondary triggers, indicating that DNA ejection mediated by a single protein can occur. The existence of gpJ mutants which can overcome the secnd triggering event provide furhter evidence that DNA ejection mediated by a single protein can occur.

The present invention is based on the discovery of a selection strategy for mutagenizing a bacteriophage tail fiber protein, particularly the tail fiber protein of lambda encoded by the gpJ gene, and positively selecting for those tail fiber mutants that can inject their nucleic acid payload into eukaryotic cells. This selection strategy can be used to select mutants that preferentially "infect" different tissue types, thereby conferring targeting capabilities to the phage.

As discussed above, lamboid phages typically interact with transmembrane proteins. Bacterial porins are channel-forming proteins found in the prokaryotic outer membrane [see Rosenbush, J. P. (1990), *Experientia*, vol. 46, pp:167–173]. These proteins function as general diffusion pores, allowing molecules less than about 600 Da into the periplasm. In *E. coli*, four different porins are known. OmpF and OmpC are the most abundant and have only non-specific transport properties. PhoE and lamB are specialized porins in that each facilitates the diffusion of specific molecules into the cell in addition to serving as an unspecific pore. The transport specificities for these two porins are: polyphosphates for PhoE and maltodextrins for lamB. When functioning as specific transporters, these porins allow molecules to pass through that are much larger than the molecular weight cutoff for their general diffusion function. The porins are also used as receptors by bacteriophage for phage binding and DNA transport. The most notable is lamB, the lambda receptor.

The porins share the same basic structure. They are homotrimers, with each monomer forming a channel in the complex. The three channels are thought to converge and merge into a single channel at the periplasmic surface (except in the case of OmpC, where the three channels appear not to merge). Porins have an unusual secondary structure among membrane proteins in that they are composed entirely of B-sheets. The porin molecules are very stable. They are soluble in detergents, and can be readily purified in active form.

The lamB Porin

The lamB pore (also called maltoporin) is an outer membrane protein from *E. coli* that functions both as a passive diffusion pore for small molecules and as a specific pore for the passage of maltose and maltodextrins [Szmelcman, et al. (1975), *J. Bacteriol.*, vol. 124, pp:112–118]. It is also the receptor for bacteriophage lambda [Randall-Hazelbauer, et al. (1973), *J. Bacteriol.*, vol. 116, pp:1436–1446]. As mentioned above, three identical copies of the lamB gene product assemble to form the native pore. Each subunit (MW ~48,000 daltons) is a pore in itself, although the monomers only function when part of the complete trimer. While the overall structure of lamB is similar to that of the other porins, its primary sequence is only distantly related, whereas ompF, ompC and phoE all have highly similar amino acid sequences.

A protein folding model for lamB is available that predicts which portions of the mature protein reside on the external and periplasmic surfaces of the membrane [Charbit, et al. (1991), *J. Bacteriol.*, vol. 173, pp:262–275]. Genetic analyses have revealed the residues involved in maltodextrin transport as well as those involved in bacteriophage lambda binding [reviewed by Charbit, et al. (1988), *J. Mol. Biol.*, vol. 201, pp:487–496]. The lamB protein has been crystallized and a low resolution (25 angstrom) structure derived [Lepault, et al. (1988) *EMBO J.*, vol. 7, pp:261–268]. The high resolution structure of an unrelated porin from *Rhodobacter capsulatus* shows several similarities to the lamB structure [Weiss, et al. (1991), *Science*, vol. 254, pp:1627–1630], and as such serves as a useful pore model.

In a preferred embodiment of the invention, the structural protein that is modified is the tail fiber protein. It is through tail fiber proteins that bacteriophages normally interact with host cells by way of specific receptors present on the surface of prokaryotic microorganisms. Tail fiber proteins define the host range specificity of a particular bacterophage. Modification of a tail fiber protein according to the invention enables a bacteriophage incorporating such protein to specifically interact with and deliver a nucleic acid molecule into a eukaryotic cell. The nucleic acid so delivered encodes a molecule capable of producing a therapeutic benefit after expression.

The present invention provides compositions and methods comprising various vectors which may be incorporated or packaged into infectious, modified bacteriophage particles (containing a mutant gpJ tail fiber protein). Such vectors may be delivered to eukaryotic cells following specific interaction with the phage particle. "Specific interaction" refers to binding to particular eukaryotic cells in a manner that allows DNA carried by the phage particle to be delivered thereto, but not to some other type of eukaryotic cell.

In the broadest terms, the vectors useful in the practice of the invention comprise a transcriptional promoter/enhancer or locus defining element(s), or other elements which control gene expression by other means such as alternate splicing, nuclear RNA export, post-translational modification of messenger RNA, or post-transcriptional modification of protein. Optionally, the vector construct may also include a signal which directs polyadenylation, as well as one or more restriction sites and a translation termination sequence. In addition, nucleic acid molecules coding for a selectable marker are neither required nor preferred.

A variety of promoters may be used in the vectors of the invention. These include, but are not limited to, the cytomegalovirus major immediate early promoter (CMV MIE), the early and late SV40 promoters, the adenovirus major late promoter, thymidine kinase or thymidylate synthase promoters, α or β interferon promoters, event or tissue specific promoters, etc. Promoters may be chosen so as to potently drive expression or to produce relatively weak expression, as desired. As those in the art will appreciate, numerous RNA polymerase II and RNA polymerase III dependent promoters can be utilized in practicing the invention.

In one embodiment, recombinant vectors of the invention comprise heterologous nucleic acid molecules (sometimes referred to herein as "exogenous" nucleic acid molecules or sequences) under the transcriptional control of an event-specific promoter, such that upon activation of the event-specific promoter the gene of interest encoded by the heterologous nucleic acid molecule is expressed. Numerous event-specific promoters may be utilized within the context of the present invention, including, without limitation, promoters which are activated by cellular proliferation (or are otherwise cell-cycle dependent) such as the thymidine kinase or thymidylate synthase promoters (Merrill, *Proc. Natl. Acad. Sci. USA*, 86:4987, 1989; Deng, et al., *Mol. Cell. Biol.*, 9:4079, 1989); or the transferrin receptor promoter, which will be transcriptionally active primarily in rapidly proliferating cells (such as hematopoietic cells) which contain factors capable of activating transcription from these promoters preferentially to express and secrete factor VIII into the blood stream; promoters such as the α or β interferon promoters which are activated when a cell is infected by a virus (Fan and Maniatis, *EMBO J.*, 8:101, 1989; Goodbourn, et al., *Cell*, 45:601, 1986); and promoters which are activated by the presence of hormones, e.g., estrogen response promoters. See Toohey et al., *Mol. Cell. Biol.*, 6:4526, 1986.

In another embodiment, vectors are provided which comprise a heterologous nucleic acid molecule under the transcriptional control of a tissue-specific promoter, such that upon activation of the tissue-specific promoter the factor VIII gene is expressed. A wide variety of tissue-specific promoters may be utilized within the context of the present invention. Representative examples of such promoters include: liver-specific promoters, such as Phospho-Enol-Pyruvate Carboxy-Kinase ("PEPCK") (Hatzoglou, et al., *J. Biol. Chem.*, 263:17798, 1988; Benvenisty, et al., *Proc. Natl. Acad. Sci. USA*, 86:1118, 1989; Vaulont, et al., *Mol. Cell. Biol.*, 6:4409, 1989), the alcohol dehydrogenase promoter (Felder, *Proc. Natl. Acad. Sci. USA*, 86:5903, 1989), and the albumin promoter and the alphafetoprotein promoter (Feuerman, et al., *Mol. Cell. Biol.*, 9:4204, 1989; Camper and Tilghman, *Genes Develop.*, 3:537, 1989); B cell specific promoters such as the IgG promoter; pancreatic acinar cell specific promoters such as the elastase promoter (Swift, et al., *Genes Develop.*, 3:687, 1989) and promoters which are specific for b cells of the pancreas, such as the insulin promoter (Ohlsson, et al., *Proc. Natl. Acad. Sci. USA*, 85:4228, 1988; Karlsson, et al., *Mol. Cell. Biol.*, 9:823, 1989); breast epithelial specific promoters such as the casein promoter (Doppler, et al., *Proc. Natl. Acad. Sci. USA*, 86:104, 1989) and the whey (wap) promoter; promoters which regulate skeletal muscle such as the myo-D binding site (Burden, *Nature*, 341:716, 1989; Weintraub, et al., *Proc. Natl. Acad. Sci. USA*, 86:5434, 1989); promoters which are specific for the pituitary gland, such as the growth hormone factor promoter (Ingraham, et al., *Cell*, 55:519, 1988; Bodner, et al., *Cell*, 55:505, 1988); promoters which are specific for melanosomes, such as the tyrosine hydroxylase promoter; T-cell specific promoters such as the T-cell receptor promoter (Anderson, et al., *Proc. Natl. Acad. Sci. USA*, 85:3551, 1988; Winoto and Baltimore, *EMBO J.*, 8:29, 1989); bone-specific promoters such as the osteocalcin promoter (Markose, et al., *Proc. Natl. Acad. Sci. USA*, 87:1701, 1990; McDonnell, et al., *Mol. Cell. Biol*, 9:3517, 1989; Kerner, et al., *Proc. Natl. Acad. Sci. USA*, 86:4455, 1989), the IL-2 promoter, IL-2 receptor promoter, and the MHC Class II promoter, and hematopoietic tissue specific promoters, for instance erythroid specific-transcription promoters which are active in erythroid cells, such as the porphobilinogen deaminase promoter (Mignotte, et al., *Proc. Natl. Acad. Sci. USA*, 86:6458, 1990), a or b globin specific promoters (van Assertdelft, et al., *Cell*, 56:969, 1989, Forrester, et al., *Proc. Natl. Acad. Sci. USA*, 86:5439, 1989), endothelial cell specific promoters such as the vWf promoter, magakaryocyte specific promoters such as b-thromboglobulin, and many other tissue-specific promoters.

Vectors according to the invention may also contain an enhancer sequence, e.g., a CMV or SV40 enhancer operably associated with other elements employed to regulate expression. A variety of other elements which control gene expression may also be utilized within the context of the present invention, including, for example, locus-defining elements such as those from the β-globin gene and CD2, a T cell marker. In addition, elements which control expression at the level of splicing, nuclear export, and/or translation may also be included in the vectors. Representative examples include the β-globin intron sequences, the rev and rre elements from HIV-1,the constitutive transport element (CTE) from Mason-Pfizer monkey virus (MPMV), a 219 nucleotide sequence that allows rev-independent replication of rev-negative HIV provital clones, and a Kozak sequence. Rev protein functions to allow nuclear export of unspliced and singly spliced HIV RNA molecules. The MPMV element allows nuclear export of intron-containing mRNA. The CTE element maps to MPMV nucleotides 8022–8240 a (Bray, et al., *Biochemistry*, 91:1256, 1994).

In another preferred embodiment, the vector contains one or more splice donor (SD) site and a splice acceptor (SA) sites to promote efficient mRNA processing and stability.

Additionally, the vectors described above contain a heterologous nucleic acid molecule. Typically, such vectors contain a heterologous nucleic acid molecule of greater than 100 nucleotides, frequently more than 3 kb, although sometimes even greater than 5 kb, or even 8 kb. In various embodiments, the heterologous nucleic acid molecule encodes a protein selected from the group consisting of IL-1, IL-2, IL- 3, IL-4, IL-5, IL-6, IL-7, IL-8, IL-9, IL-10, IL-11, IL-12, IL-13, IL-14, IL-15, an α-IFN, a γ-IFN, G-CSF, GM-CSF, SCF, MGDF, EPO, the flk-2 ligand, factor VIII, and factor IX. Within other embodiments of the invention, the heterologous nucleic acid molecule may encode a lymphokine receptor. Representative examples of such receptors include receptors for any of the lymphokines set forth above.

In still other embodiments, the gene transfer systems of the invention include a selected heterologous nucleic acid molecule which may be obtained from a virus selected from the group consisting of influenza virus, HPV, HBV, HCV, EBV, HIV, HSV, FeLV, FIV, Hanta virus, HTLV I, HTLV II and CMV. Within one preferred embodiment, the heterologous sequence obtained from HPV encodes a protein selected from the group consisting of E5, E6, E7 and L1.

In yet other embodiments, the vectors described above include a selected heterologous nucleic acid molecule encoding an HIV protein selected from the group consisting of HIV gp120 and gag.

The selected heterologous nucleic acid molecules described above may also encode one or more antisense molecules, noncoding sense molecules, and/or ribozymes. In preferred embodiments the antisense or noncoding sense sequence is selected from the group consisting of sequences which are complementary to influenza virus, HPV, HBV, HCV, EBV, HIV, HSV, FeLV, FIV, Hanta virus, HTLV I, HTLV II, and CMV sequences.

In another aspect, the present invention provides recombinant bacteriophage particles which, upon introduction into a eukaryotic cell, produce an infected cell which is viable for at least 24 hours after infection, wherein the particles also carry a vector construct which directs the expression of at least one antigen or modified form thereof in target cells infected with the phage particle, the antigen or modified form thereof being capable of stimulating an immune response within an animal. In various embodiments, the expressed antigen or modified form thereof elicits a cell-mediated immune response, preferably an HLA class I-restricted immune response.

In still another aspect, the present invention provides recombinant phage particles which carry a vector capable of directing the expression of a palliative (i.e., a compound affording relief, but not a cure) in cells infected with the phage particle, the palliative being capable of inhibiting a function of a pathogenic agent necessary for pathogenicity. In various embodiments, the pathogenic agent is a virus, fungi, protozoa, or bacteria, and the inhibited function is selected from the group consisting of adsorption, replication, gene expression, assembly, and exit of the pathogenic agent from infected cells. In other embodiments, the pathogenic agent is a cancerous cell, cancer-promoting growth factor, autoimmune disorder, cardiovascular disorders such as restenosis, osteoporosis and male pattern baldness, and the inhibited function is selected from the group consisting of cell viability and cell replication. In further embodiments, the vector directs the expression of a toxic palliative in infected target cells in response to the presence in such cells of an entity associated with the pathogenic agent; preferably the palliative is capable of selectively inhibiting the expression of a pathogenic gene or inhibiting the activity of a protein produced by the pathogenic agent. In still further embodiments, the palliative comprises an inhibiting polypeptide specific for viral protease, an antisense RNA complementary to RNA sequences necessary for pathogenicity, a sense RNA complementary to RNA sequences necessary for pathogenicity, or a defective structural protein of a pathogenic agent, such protein being capable of inhibiting assembly of the pathogenic agent.

In yet further embodiments, phage particles of the invention direct the expression of a palliative and, more particularly, direct the expression of a gene product capable of activating an otherwise inactive precursor into an active inhibitor of the pathogenic agent, for example, the herpes thymidine kinase gene product, a tumor suppressor gene, or a protein that activates a compound with little or no cytotoxicity into a toxic product in the presence of a pathogenic agent, thereby effecting localized therapy to the pathogenic agent [U.S. Ser. No. 08/155,994 now U.S. Pat. No. 5,380,283]. Alternatively, the phage particle directs the expression of a protein that is toxic upon processing or modification by a protein derived from a pathogenic agent, a reporting product on the surface of target cells infected with the bacteriophage and containing the pathogenic agent, or an RNA molecule which functions as an antisense or ribozyme specific for a pathogenic RNA molecule required for pathogens.

In yet a further aspect, the present invention provides bacteriophage particles which direct the expression of a gene capable of suppressing one or more elements of the immune system in target cells infected with the phage, and a phage particle which directs the expression of a blocking element in cells infected with the phage, the blocking element being capable of binding to either a receptor or an agent such that the receptor/agent interaction is blocked.

In still further aspects, methods are provided for administering any of the above-described bacteriopohage particles or vectors contained therein for a prophylactic or therapeutic effect. For example, one aspect the present invention provides methods of stimulating an immune response to an antigen, comprising the step of infecting susceptible target cells with a bacteriophage particle which directs the expression of at least one antigen or modified form thereof in target cells infected with the phage, the antigen or modified form thereof being capable of stimulating an immune response within an animal. In one embodiment, the target cells are infected in vivo, although within other embodiments the target cells are removed, infected ex vivo, and returned to the animal.

In still further aspects of the present invention, methods of stimulating an immune response to a pathogenic antigen are provided, comprising the step of infecting susceptible target cells with an phage particle which directs the expression of a modified form of a pathogenic antigen in target cells infected with the phage the modified antigen being capable of stimulating an immune response within an animal but having reduced pathogenicity relative to the pathogenic antigen.

In even further aspects of the present invention, methods of stimulating an immune response to an antigen are provided, comprising infecting susceptible target cells with a phage particle which directs the expression of a polypeptide having multiple epitopes, one or more of the epitopes derived from different proteins.

In yet another aspect of the invention, methods of stimulating an immune response within a warm-blooded animal are provided, comprising infecting susceptible target cells associated with a warm-blooded animal with nucleic acid sequences coding for either individual class I or class II MHC protein, or combinations thereof, and infecting the cells with a phage particle which directs the expression of at least one antigen or modified form thereof in target cells infected with the phage particle, the antigen or modified form thereof being capable of stimulating an immune response within the animal.

In another aspect of the present invention, methods of inhibiting a pathogenic agent are provided, comprising infecting susceptible target cells with an phage particle which directs the expression of a palliative in cells infected with the phage particle, the palliative being capable of inhibiting a function of a pathogenic agent necessary for pathogenicity.

As utilized within the context of the present invention, "vector" or "vector construct" which direct the expression of a heterologous gene or nucleic acid sequence of interest refers to nucleic acid molecule which directs the expression of the heterologous gene or sequence of interest. In addition, although "eukaryotes" are generally referred to, it should be understood that the present invention may be readily applied to a wide variety of eukaryotes, including plants and animals (both mammalian and non-mammalian), including for example, humans, chimps, macaques, cows, horses, sheep, dogs, birds, cats, fish, rats, and mice. Further, although phage such as lambda may be specifically described herein, it should be understood that a wide variety of other bacteriophages may also be utilized.

Within other aspects of the present invention, methods are provided for delivering a heterologous nucleic acid sequence to an animal comprising the steps of administering to the warm-blooded animal a eukaryotic layered vector initiation system, as described below.

In one embodiement of the invention, alphavirus derived layered DNA vector constructs, for example those derived from Sindbis virus, may be inserted into a lambda vector according to the invention. The resulting vector and then packaged into mature phage particles in vitro, using a packaging extract containing the modified gp J protein tail fiber which permits the infection of eukaryotic cells. The layered alphavirus DNA vector construct contains, for example, an RNA polymerase II expression cassette with the capacitiy for directing the synthesis of an alphvirus derived RNA vector. In such a configuration, primary transcription of the delivered lambda vector occurs in the nucleus, followed by transport and autocatalytic amplification of the vector RNA in the cytoplasm according to the alphavirus replication strategy, infra. The autocatyltic amplification nature of the vector RNA results in a high level of heterologous gene expression Sindbis virus is the prototype member of the alphavirus genus of the Togavirus family. The genomic RNA (49S RNA) of alphaviruses is unsegmented, of positive polarity, approximately 11–12 kb in length, and contains a 5' cap and a 3' polyadenylated tail. During viral replication, the genomic 49S RNA serves as template for synthesis of the complementary negative strand. The negative strand in turn serves as template for genomic RNA and for an internally initiated 26S subgenomic RNA. The non-structural proteins are translated from the genomic RNA. Alphaviral structural proteins are translated from the subgenomic 26S RNA. All vital genes are expressed as a polyprotein and processed into individual proteins by proteolytic cleavage post translation.

The nature of viruses having an RNA genome with positive polarity is such that when introduced into a eukaryotic cell, the genomic nucleic acid serves as a functional message RNA (mRNA) molecule. Thus, genomic RNA purified from the virus can initiate the same infection cycle which is characteristic of infection by the wild type virus from which the RNA was purified. It is this property that has led to the development of alphavirus based heterologous gene expression vectors. These systems employ replacement vectors, in which the Sindbis viral structural genes are substituted with heterologous genes of interest.

It is well known that DNA molecules having the appropriate signals can replicate in vivo when introduced directly into animals (Dubensky et al., *PNAS* 81:7429–7533, 1984). Administration of Sindbis cDNA vectors directly as DNA molecules is feasible in some applications in which the Sindbis directed expression of therapeutic genes have a trans effect. These applications include immunomodulation and expression of cytokines or other therapeutic proteins.

Described in U.S. Ser. No. 08/348,472, now abandoned, is the development of a Eukaryotic Layered Vector initiation System (ELVIS), in which a primary transcript, corresponding to the first layer, is synthesized from an RNA polymerase II promoter following introduction into the host cell. The second layer of the vector is activated once the primary transcript is transported to the cytoplasm where the translation of the Sindbis nonstructural proteins occurs. The nonstructural proteins catalyze the amplification of the transported RNA and the production of high levels of the subgenomic mRNA via the mechanism employed by the wild-type virus. The subgenomic mRNA, which contains the therapeutic gene is effeciently translated, resulting in high levels of expressed protein. The ELVIS constructions are comprised of the following ordered elements: a 5' eukaryotic promoter capable of initiating the synthesis of viral RNA at the authentic Sindbis 5' end, a 5' sequence which is capable of initiating transcription of a Sindbis virus, a nucleotide sequence encoding Sindbis non structural proteins, a vital junction region, a heterologous sequence, a Sindbis RNA polymerase recognition sequence, and a 3' transcription termination polyadenylation signal sequence. The eukaryotic Sindbis cDNA expression vector may include also intervening sequences (introns), which are spliced from the pre-RNA in the nucleus prior to transport to the cytoplasm, and which may improve the overall efficiency of the system, in terms of molecules of functional mRNA transported to the cytoplasm/nuclear DNA template. The intron splicing signals are located, for example, between Sindbis and heterologous gene regions. Expression of reporter proteins, for example luciferase and b-galactocidase, as well as viral antigens, for example HBV core has been demonstrated in cells transfected with ELVIS vectors, supporting the notion that ELVIS vectors would function according to design when inserted into lambda vectors, which when packaged can infect eukaryotic cells due to a modified gp J tail fiber.

Within one embodiment, the construct within the eukaryotic layered vector initiation systems of the present invention is an alphavirus vector construct. Within other embodiments, the construct is derived from a virus selected from the group consisting of poliovirus, rhinovirus, coxsackieviruses, rubella, yellow fever, HCV, TGEV, IBV, MHV, BCV, parainfluenza virus, mumps virus, measles virus, respiratory syncytial virus, influenza virus, RSV, MoMLV, HIV, HTLV, hepatitis delta virus and Astrovirus. Within yet other embodiments, the promoter which is capable of initiating the 5' synthesis of RNA from cDNA is selected from the group consisting of the MoMLV promoter, metallothionein promoter, glucocorticoid promoter, SV40 promoter, and the CMV promoter. Within further embodiments, the eukaryotic layered vector initiation systems further comprise a polyadenylation sequence.

In further embodiments of the invention, in any of the above aspects the alphavirus cDNA vector construct may be derived from an alphavirus selected from the group consisting of Aura, Fort Morgan, Venezuelan Equine Encephalitis, Ross River, Semliki Forest, Sindbis, and Mayaro.

Representative promoters suitable for use within the present invention include both eukaryotic (e.g., recognized by RNA polymerase I, II, or III) and prokaryotic promoters, and inducible or non-inducible (i.e., constitutive) promoters, such as, for example, murine leukemia virus promoters (e.g., MoMLV), metallothionein promoters, the glucocorticoid promoter, Drosophila actin 5C distal promoter, SV 40 promoter, heat shock protein 65 promoter, heat shock protein 70 promoter, immunoglobulin promoters, mouse polyoma virus promoter (Py), rous sarcoma virus (RSV), BK virus and JC virus promoters, MMTV promoter, alphavirus junction region, CMV MIE promoter, adenovirus VA1RNA, rRNA promoter, tRNA methionine promoter and the lac promoter. The second layer comprises a construct which is capable of expressing one or more heterologous nucleotide sequences, and of replication in a cell either autonomously or in response to one or more factors. Within one embodiment of the invention, the second layer construct may be an alphavirus vector construct as described above.

A wide variety of vector systems may be utilized as the first layer of the eukaryotic layered vector initiation system, including for example, viral vector constructs developed from DNA viruses such as those classified in the Poxviridae, including for example canary pox virus or vaccinia virus (e.g., Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330 and 5,017,487; WO 89/01973); Papoviridae such as BKV, JCV or SV40 (e.g., Mulligan et al., *Nature* 277:108–114, 1979); Adenoviridae such as adenovirus (e.g., Berkner, *Biotechniques*. 6:616–627, 1988; Rosenfeld et al., *Science* 252:431–434, 1991); Parvoviridae such as adeno-associated virus (e.g., Samulski et al., *J. Vir.* 63:3822–3828, 1989; Mendelson et al., *Virol.* 166:154–165, 1988; PA 7/222,684); Herpesviridae such as Herpes Simplex Virus (e.g., Kit, *Adv. Exp. Med. Biol.* 215:219–236, 1989); and Hepadnaviridae (e.g., HBV), as well as certain RNA viruses which replicate through a DNA intermediate, such as the Retroviridae (see, e.g., U.S. Pat. No. 4,777,127, GB 2,200,651, EP 0,345,242 and WO91/02805; Retroviridae include leukemia in viruses such as MoMLV and immunodeficiency viruses such as HIV, e.g., Poznansky, *J. Virol.* 65:532–536, 1991).

Similarly, a wide variety of vector systems may be utilized as second layer of the eukaryotic layered vector initiation system, including for example, vector systems derived from viruses from the families: Picornaviridae (e.g., poliovirus, rhinovirus, coxsackieviruses), Caliciviridae, Togaviridae (e.g. alphavirus, rubella), Flaviviridae (e.g., yellow fever), Coronaviridae (e.g., HCV, TGEV, IBV, MHV, BCV), Rhabdoviridae, Filoviridae, Paramyxoviridae (e.g., parainfluenza virus, mumps virus, measles virus, and respiratory syncytial virus), Orthomyxoviridae (e.g., influenza virus), Bunyaviridae, Arenaviridae, Retroviridae (e.g., RSV, MoMLV, HIV, HTLV), hepatitis delta virus and Astrovirus. In addition, non-mammalian RNA viruses (as well as components derived therefrom) may also be utilized, including for example, bacterial and bacteriophage replicases, as well as components derived from plant viruses such as Topamoviruses and Bromoviruses (see Strauss et al., *Micro. Rev.* 58:491–562, 1994).

Production Of Phage Capable of Specific Eukaryotic Cell Interaction

To produce bacteriophage particles capable of specifically interacting with eukaryotic cells for the purpose of gene delivery, any of a variety of techniques may be utilized to mutagenize or otherwise alter the nucleotide sequence of one or more genes coding for bacteriophage structural proteins. Following mutagenesis, screening is performed to identify mutants possessing the desired changes.

A. Mutagensis

The advent of recombinant DNA technology has enabled mutagenesis of cloned DNA molecules by various chemical and enzymatic methods. Techniques include random, saturation, and site-directed mutagenesis. Random mutagenesis is typically performed by using known chemical mutagens or radiation according to known methods to randomly introduce mutations within a specific region. The mutation rate will depend on the amount of mutagen used. In saturation mutagenesis, procedures are employed to introduce all possible mutations within a particular region. In site-directed mutagensis (conducted using either oligonulceotides or PCR), one or more specific nucleotide changes can be introduced into particular DNA sequence. As those in the art will recognize, other techniques, such as linker scanning mutagenesis, may also be employed in the practice of this invention.

In a prefered embodiment of this invention, PCR stauration mutagenesis is employed.

B. Screening Techniques

After one or more mutants have been generated, it is necessary to select those having the desired phenotype, namely the ability to specifically interact with an animal cell for purposes of delivering a nucleic acid molecule thereto.

After identifying one or more mutants with the desired phenotype, the nucleic acid molecule encoding the mutated protein responsible for the altered phenotype is isolated and characterized, as is the protein. Characterization involves sequencing the nucleic acid molecule and comparing it to the wild type nucleotide sequence to identify any change(s). The putative amino acid sequence is also deduced and compared to that of the wild type protein.

In a preferred embodiment of the invention, lambda particles incorporating mutant gpJ proteins are identified on the basis of their ability to confer antibiotic resistence to eukaryotic cells.

Lambda Production Systems

As those in the art will appreciate, a number of different production systems can be used to produce bacteriophage particles in accordance with the present invention. As discussed above, the ability to produce in vivo viral stocks having high titers, e.g., $1 \times 10^{10}$ cfu/mL, as well the ability to utilize in vitro packaging systems, is a major advantage in the production of gene transfer systems, as compared to existing retrovirus, adenovirus, and pox virus systems.

A. In Vitro production

The in vitro packaging of DNA into infectious bacteriophage lambda was initially developed by Becker et al. (*PNAS* 72:581, 1975) using mixtures of extracts prepared from bacteria infected with lambda mutant in genes required for assembly of bacteriophage particles. The procedure has been modified to yield efficiencies of $10^8$–$10^9$ pfu/mg of intact bacteriophage lambda in a highly reproducible manner. Approximately 0.05 to 0.5% of the DNA molecules present in the reaction can be packaged into infectious virions (reviewed in Sambrook et al., in Molecular Cloning, A Laboratory Manual, Cold Spring Harbor Laboratory Press, 1989).

The E protein, the major component of the bacteriophage head is required for the assembly of the earliest identifiable precursor. Bacteriophages having mutantions in the E gene accumulate all of the components of the viral capsid. The D protein is localized on the outside of the bacteriophage head and is involved in the coupled process of insertion of bacteriophage lambda DNA into the "prehead" precursor and the subsequent maturation of the head. Bacteriophages having mutantions in the D gene accumulate the immature prehead but do not allow insertion of bacteriophage lambda DNA into the head. The A protein is involved in the insertion of DNA into the bacteriophage prehead and cleavage of concatenated precursor DNA at the cos sites bordering the genome to be packaged. Extracts are usually prepared from cells containing lambda lysogens of the appropriate genotype, that is, amber mutations in the A, D, or E gene, as well as lysogens that carry one or more of the following mutations: cIts857 or imm434 cIts, which specify a temperature-sensitive lambda repressor molecule; Sam7, an amber mutation in the bacteriophage S gene that is required for cell lysis; b-region deletion (b2 or b1007), a deletion in the bacteriophage genome that removes the DNA attachment site (att); and red3 (in lambda) and recA (in *E. coli*), mutations that inactivate the generalized recombination systems of lambda and the host.

Packaging extracts are available from commercial sources, e.g., Gigapack® extracts (Stratagene, La Jolla, Calif.). However, they can also be prepared by growing the appropriate lysogenic bacteria to mid-log phase at 32° C., inducing lytic functions by inactivating the cI repressor protein by raising the temperature to 45° C. for 15 minutes, and then growing the cultures for an additional 2–3 hours at 38°–39° C. to allow packaging components to accumulate. Cell extracts are then prepared. (Sambrook et al., supra)

Other protocols are also available for the preparation of packaging extracts. One such method involves lysogens having b-region deletions to provide complementing components of the packaging reaction. Such lySogens are grown and induced separately. Extracts of each culture are prepared and blended into a mixture that contains all of the components necessary for packaging of suitable DNA. Neither lysogen alone is capable of packaging exogenously added DNA. The protocol is highly reproducible, and it results in packaging mixtures that are efficient and free from background (when assayed on hosts that are non-suppressing).

Another method involves a single lysogen to prepare packaging extracts. Induction of the lysogen results in the intracellular accumulation of all protein components needed for packaging, and complete preheads are formed. However, the next steps in the packaging process are the recognition of the cos sites on the concatenated bacteriophage 1 DNA by the bacteriophage A protein and the insertion of the phage genome into the prehead. The lack of the cos site in the prophage DNA prevents this step from occurring, and packaging is thus effectively halted at the prehead stage, even though all necessary components that are used later in the process are present. Cell extracts containing the lambda packaging components are then prepared. Exogenous DNA with an active cos site can then be inserted into the prehead in the presence of ATP, resulting in the production of infectious bacteriophage particles. Phage produced from extracts made in this way usually generate a lower background of plaques than binary packaging systems, because the deletion of the cos site blocks packaging of endogenous bacteriophage lambda DNA more completely than does the deletion of the b region.

In a preferred embodiment of this apsect of the invention, packaging components and extracts are purified uding any of a number of well known purification procedures. Additionally, because infectious phage particles produced from these extracts, those intended for administration to animals, particularly humans, for therapeutic purposes should be endotoxin free.

B. Improvements

After a suitable tail fiber protein is identified and specific tail packaging extracts are generated, vectors can be generated to take advantage of the increased packaging ability conferred by cosmid vectors. Such vectors contain the cos site from lambda and an origin of replication and can incorporate DNA payloads of up to 50 kb. The vector may be modified to take advantage of the tissue specificity of the tail fiber/receptor interaction and confer an additional level of regulation on the gene transfer system by incorporating tissue specific promoters, enhancers, and other regulatory elements. According to this invention, a bacteriophage-mediated gene transfer system injects a linear nucleic acid molecule, preferably DNA, into the cytoplasm of a eukaryotic cell. For protein expression to occur, the injected DNA must travel to the nucleus where it can serve as a substrate for DNA dependent RNA polymerase transcription or stably integrate into the host chromatin, with the latter likely occurring at a low frequency. Further modifications can be engineered to enhance gene delivery functions, such as inclusion of sequences designed to confer episomal stability and replication in eukaryotic cells and to enhance stability and maintenance of such vectors in eukaryotic cells.

Episomal stability may be provided by incorporation of oriP and EBNA-1 sequences from EBV into vectors useful in the practice of the invention. Such modifications may confer long term stability and gene expression in the target cells.

Addition of telomeric sequences to enhance stability and maintenance of vectors in eukaryotic cells is also envisioned. In this embodiment, telomeric repeats are inserted before the cos sites. In addition, one or nucleic molecules coding for a a centromeric sequence may be included in the vector to be packaged. Centromeres are required for correct segregation during cell division, and regions of about 120 bp in size that confer sergregation stability have been described.

Targeting Via Chimeric Tail Proteins

An alternative approach to mutagenizing bacteriophage proteins to specifically target eukaryotic cells via unknown receptors involves engineering targeting specificity into the phage gene transfer system. This may be accomplished by incorporating "simple" ligands into phage proteins such as the the gpJ tail fiber protein or other tail proteins (e.g., gpV, gpH) of lambda phage. A "simple" ligand is defined as a ligand in which a receptor binding domain is encoded by the primary sequence of amino acids and does not require protein folding of distal elements to confer receptor binding.

The bacteriophage lambda gene V encodes the major tail protein gpV that forms the tubular part of the phage tail. The tail consists of 32 stacked disks, with each disk being made up of six gpV subunits. gpV is comprised of 246 amino acids with a relative molecular weight of 25.8 kD. The protein has two domains, with the smaller C-terminal domain (about 70 amino acids) being located toward the outside of the tail tube. Normally functioning V gene mutants have been identified that lack up to one third of gpV, essentially the small C-terminal domain. Maruyama, et al. [(1994), *Proc. Nat'l Acad. Sci. USA*, vol. 91, pp:8273–8277] reported that such C-terminal mutantions could be used to make chimeric, or "fusion," proteins that are incorporated to functional phage particles and presented on the surface of the phage tail tubes. Maruyama, et al.'s constructs incorporated a repetitive Pro-Thr spacer sequence between the C-terminus of the truncated gpV protein and the foreign protein. The spacer sequence was designed to prevent interference between the two parts of the chimera, provide sites for endopeptidase cleavage, e.g., by C. fimi exo- and endo-glucanase, and collagenase, and to provide for cellulose binding. This or similar approaches can be employed in the context of the present invention to provide .cell or tissue specific targeting. For instance, chimeric proteins comprising cell-specific ligands, i.e., peptide hormones, simple liugands, cytokines, lymphokines, carbohydrates, etc., linked to all or part of gpV can be generated by techniques known in the art. Such proteins can be expressed in systems designed to produce intact lambda particles in vivo or as part of an in vitro packaging system, such as have been described above.

Shibata, et al. [(1993) *Biochimie*, vol. 75, pp:459–465] reported the production of a biological bi-functional protein comprisiing 22 amino acids (residues 1488–1509) containing the cell binding domain (Arg-Gly-Asp-Ser) of fibronectin, wherein the fibronectin domain was substituted for part of gpJ. The chimeric gpJ protein fragment, comprising (from the N-terminus) 36 amino acids from the vector, residues 180–211 of gpJ, the fibronectin sequence, amino acids 234–388 of gpJ, and 15 amino acids encoded by the vector, was expressed in *E. coli* and and showed about 10-fold higher affinity for a human retinoblast cell line than wild type gpJ.

According to this aspect of this invention, heterologous ligand sequnces may be inserted into lambda proteins. "Heterologous ligand sequences" comprise amino acid sequences which, when expressed in the correct conformation, confer affinity for one or more particular receptors. In various embodiments, the heterologous ligand sequence is selected from the group consisting of VSVG, HIV gp120, an antibody, insulin, and CD4. Also included among such ligands are peptide ligands nine amino acids in length derived from the gp350/220 envelope protein of the Epstein-Barr virus (EBV) which binds to CR2 (CD21), a eukaryotic cell surface molecule. EBV, a human g-herpes virus, is the etiological agent of infectious mononucleosis, (Henle et al. 1968), Burkitt's lymphoma (De-The and Zeng, 1982), and nasopharyngeal carcinoma (Huang et al., 1974). EBV is the most selective of the human herpes viruses, binding almost exclusively to B-cells and epithelial cells.

This selectiveness is due to the expression of CR2, which normally binds the complement protein C3dg. The ligand has the amino acid sequence EDPGFFNVE [SEQ ID NO: 1], and is easily inserted into a bacteriophage protein for expression as a receptor-specific ligand to target B cells and epithelial cells. As a result, bacteriophage particles according to the invention which incorporate this heterologous ligand sequence may be used to deliver a therapeutic molecule encoded by a vector specifically to EBV-infected cells and may be used to treat the EBV infection or the forms of cancer caused by EBV, among other diseases.

A wide variety of targeting elements may be utilized within the context of the present invention, in order to specifically direct a gene transfer system to a selected cell type. Generally, targeting elements are proteins or peptides, although other non-proteinaceous molecules may also function as targeting elements. For example, within one embodiment of the invention, antibodies may be utilized in order to target a selected cell type (see generally, Wilchek and Bayer, *Anal. Biochem* 171:1-32, 1988). Representative examples include antibodies, such as anti-CD34 (e.g., 12.8 (Andrews et al., *Blood* 67:842, 1986), and My10 (Civin et al., *J. Immunol.* 133:157, 1984; commercially available from Becton Dickinson under the designation HPCA-2), anti-CD4 antibodies to target CD4+ T-cells, anti-CD8 antibodies to target CD8+ cells, and antibodies to target cancer cells (see Alper et al., *Cell Growth Differ.* 1:591–9, 1990; King et al., *J. Biochem.* 281:317-23, 1992; Nap et al., *Canc. Res.* 52:2329-39, 1992). Antibody fragments, such as Fab, may also be employed.

Other suitable targeting elements include hormones and hormone receptors. Additionally, immune accessory molecules may be utilized to target specific receptors on various cells. Examples include interferon targeted to macrophages and natural killer cells, interleukins to T-lymphocytes, and erythropoietin and CSF to bone marrow cells.

Within yet other embodiments, other ligands and antibodies may be utilized to target selected cell types, including for example: polypeptides to target nerve cells; lectins (Sharon and Lis, *Science* 246:227, 1989); acetylated molecules to target macrophage scavenger receptors (see Brown et al., *Ann. Rev. Biochem* 52:223–261, 1983; Paulinski et al., *PNAS* 86:1372-1376, 1989); vital receptors (Haywood, *J. Vir.* 68(1):1-5, 1994); transferrin to target tumor cells (Huebers et al., *Physio. Rev.* 67:520, 582, 1987); etc.

Alternatively, targeting elements may be selected from libraries created utilizing recombinant techniques (Scott and Smith, *Science* 249:386, 1990; Devlin et al., *Science* 249:404, 1990; Houghten et al., *Nature* 354:84 1991; Matthews and Wells, *Science* 260:1113,1993; Nissim et al., *EMBO J.* 13(3):692–698, 1994), or equivalent techniques utilizing organic compound libraries.

The present invention also provides a wide variety of high affinity binding pairs that can be used as targeting elements. Representative examples of suitable affinity binding pairs include biotin/avidin with an affinity $(K_D)$ of $10^{-15}$M (Richards, Meth. Enz. 184:3–5, 1990; Green, *Adv. in Protein Chem.* 29:85, 1985); cytostatin/papain with an affinity of $10^{-14}$M (Bjork and Ylinenjarvi, *Biochemistry* 29:1770-1776, 1990); val-phosponate/carboxypeptidase A with an affinity of $10^{-14}$M (Kaplan and Bartlett, *Biochemistry* 30:8165–8170, 1991); 4CABP-RuBisCo with an affinity of $10^{-13}$M, (Schloss, *J. Biol. Chem.* 263:4145–4150, 1988); and tobacco hornworm diuretic hormone/tobacco hornworm diuretic hormone receptor, with an affinity of $10^{-11}$M (Reagan et al., *Arch. Insect Biochem. Physiol.* 23:135–145, 1993).

A wide variety of other high affinity binding pairs may also be developed, for example, by preparing and selecting antibodies which recognize a selected antigen, and by further screening of such antibodies in order to select those with a high affinity (see generally, U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Alternatively, antibodies or antibody fragments may also be produced and selected utilizing recombinant techniques (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in Escherichia coli for Generation of Monoclonal Catalytic Antibodies: Construction of a Heavy Chain Variable Region-Specific cDNA Library," *Proc. Natl. Acad. Sci. USA* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques).

As noted above, the present invention provides recombinant bacteriophage particles carrying vectors and methods of using such vectors for the treatment of a wide variety of pathogenic agents. Within one aspect of the invention, recombinant vectors are provided which direct the expression of a gene product capable of activating an otherwise inactive precursor into an active inhibitor of a pathogenic agent. As will be evident to one of skill in the art, a wide variety of inactive precursors may be converted into active inhibitors of a pathogenic agent. For example, antiviral nucleoside analogues such as AZT or ddC are metabolized by cellular mechanisms to the nucleotide triphosphate form in order to specifically inhibit retroviral reverse transcriptase, and thus viral replication (Furmam et al., *Proc. Natl. Acado Sci. USA* 83:8333–8337, 1986). Nucleic acid molecules delivered by bacteriophage as described herein which direct the expression of a gene product (e.g., a protein) such as Herpes Simplex Virus Thymidine Kinase (HSVTK) or Varicella Zoster Virus Thymidine Kinase (VZVTK) which assists in metabolizing antiviral nucleoside analogues to their active form are therefore useful in activating nucleoside analogue precursors (e.g., AZT or ddC) into their active form.

Within a related aspect of the present invention, nucleic acid molecules (or vectors) are provided which direct the expression of a gene product that activates a compound with little or no cytotoxicity into a toxic product. Briefly, a wide variety of gene products which either directly or indirectly activate a compound with little or no cytotoxicity into a toxic product may be utilized within the context of the present invention. Representative examples of such gene products include HSVTK and VZVTK which selectively monophosphorylate certain purine arabinosides and substituted pyrimidine compounds, converting them to cytotoxic or cytostatic metabolites. More specifically, exposure of the drugs ganiclovir, acyclovir, or any of their analogues (e.g., FIAU, FIAC, DHPG) to HSVTK, phosphorylates the drug into its corresponding active nucleotide triphosphate form.

Representative examples of other gene products which may be utilized within the context of the present invention include: *E. coli* quanine phosphoribosyl transferase which converts thioxanthine into toxic thioxanthine monophosphate (Besnard et al., *Mol. Cell. Biol.* 7:4139–4141, 1987); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase which will convert 5-fluorocytosine to the toxic compound 5-fluorouracil (Mullen, *PNAS* 89:33, 1992); carboxypeptidase G2 which will cleave the glutamic acid from para-N-bis (2-chloroethyl) aminobenzoyl glutamic acid, thereby creating a toxic benzoic acid mustard; and Penicillin-V amidase, which will convert phenoxyacetabide, derivatives of doxorubicin and melphalan to toxic compounds (see generally, Vrudhula et al., *J. of Med. Chem.* 36(7):919–923, 1993; Kern et al., *Canc. Immun. Immunother.* 31(4):202–206, 1990).

Within a related aspect of the present invention, vectors are provided which direct the expression of a gene product that activates a compound with little or no cytotoxicity into a toxic product in the presence of a pathogenic agent, thereby affecting localized therapy to the pathogenic agent. In this case, expression of the gene product from the vector is limited to situations wherein an entity associated with the pathogenic agent, such as an intracellular signal identifying the pathogenic state, is present, thereby avoiding destruction of nonpathogenic cells. This cell-type specificity may also be conferred at the level of infection, by targeting recombinant virus carrying the vector to cells having or being susceptible to the pathogenic condition.

A wide variety of cytotoxic genes may be utilized within the context of the present invention. Representative examples include proteins such as ricin (Lamb et al., *Eur. J. Biochem.* 148:265–270, 1985), abrin (Wood et al., *Eur. J. Biochem.* 198:723–732, 1991; Evensen, et al., *J. of Biol. Chem.* 266:6848–6852, 1991: Collins et al., *J. of Biol. Chem.* 265:8665–8669, 1990; Chen et al., *Fed. of Eur. Biochem Soc.* 309:115–118, 1992), diphtheria toxin (Tweten et al., *J. Biol. Chem.* 260:10392–10394, 1985), cholera toxin (Mekalanos et al., *Nature* 306:551–557, 1983; Sanchez & Holmgren, *PNAS* 86:481–485, 1989), gelonin (Stirpe et al., *J. Biol. Chem.* 255:6947–6953, 1980), pokeweed (Irvin, *Pharmac. Ther.* 21:371–387, 1983), antiviral protein (Barbieri et al., *Biochem. J.* 203:55–59, 1982; Irvin et al., *Arch. Biochem. & Biophys.* 200:418–425, 1980; Irvin, *Arch. Biochem. & Biophys.* 169:522–528, 1975), tritin, Shigella toxin (Calderwood et al., *PNAS* 84:4364–4368, 1987; Jackson et al., *Microb. Path.* 2:147–153, 1987), and Pseudomonas exotoxin A (Carroll and. Collier, *J. Biol. Chem.* 262:8707–8711, 1987), herpes simplex virus thymidine kinase (HSVTK) (Field et al., *J. Gen. Virol.* 49:115–124, 1980), and *E. coli.* guanine phosphoribosyl transferase.

Within other embodiments of the invention, the cytotoxic gene may include an antisense molecule which inhibits, for example, tumor cell growth, viral replication, or a genetic disease by preventing the cellular synthesis of critical proteins needed for cell growth. Antisense RNA may be utilized as a cytotoxic gene in order to induce a potent Class I restricted response, as in high levels of specific antisense sequences may be utilized to induce the increased expression of interferons (including γ-interferon), due to the formation of large quantities of double-stranded RNA, which, in turn, boosts the expression of MHC Class I antigens.

Within other aspects of the invention, recombinant viral vectors are provided carrying a vector construct which directs the expression of a gene product that activates a compound with little or no cytotoxicity into a toxic product. Within preferred embodiments of the invention, the recombinant viral vectors direct the expression of a gene product that activates a compound with little or no cytotoxicity into a toxic product in the presence of a pathogenic agent, thereby affecting localized therapy to the pathogenic agent.

For example, within one embodiment of the invention, the recombinant vector directs the expression of the herpes simplex virus thymidine kinase (HSVTK) gene under the transcriptional control of an HIV promoter (known to be transcriptionally silent except when activated by HIV tat protein). Expression of the tat gene product in human cells infected with HIV and carrying the vector causes increased production of HSVTK. The cells (either in vitro or in vivo) are then exposed to a drug such as ganciclovir, acyclovir or its analogues (FIAU, FIAC, DHPG), which is phosphorylated by HSVTK (but not by cellular thymidine kinase) to their corresponding active nucleotide triphosphate forms. Those cells containing the recombinant vector and expressing HIV tat protein are selectively killed by the presence of a specific dose of these drugs.

Within one embodiment of the invention, expression of the conditionally lethal gene, such as HSVTK, may be made even more HIV-specific by including cis-acting elements in the transcript (CRS/CAR), which require an additional HIV gene product, rev, for optimal activity (Rosen et al., *Proc. Natl. Acad. Sci. USA* 85:2071, 1988). Sequences of this type (i.e., post-transcriptional regulation of gene expression) may be used for event- or tissue-specific regulation of vector gene expression. In addition, multimerization of these sequences may be utilized in order to generate even greater specificity.

In a manner similar to the preceding embodiment, vectors may be generated which carry a gene for phosphorylation, phosphoribosylation, ribosylation, or other metabolism of a purine- or pyrimidine-based drug. Such genes may have no equivalent in mammalian cells, and might come from organisms such as a virus, bacterium, fungus, or protozoan. Representative examples include: *E. coli* guanine phosphoribosyl transferase (gpt) gene product, which converts thioxanthine into thioxanthine monophosphate (see Besnard et al., *Mol. Cell. Biol.* 7:4139–4141, 1987); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase which will convert 5-fluorocytosine to the toxic compound 5-fluorouracil (Mullen, *PNAS* 89:33, 1992); carboxypeptidase G2 which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds.

The present invention provides methods and compositions suitable for inhibiting MHC antigen presentation in order to suppress the immune response of the host. Briefly, CTL are specifically activated by the display of processed peptides in the context of self MHC molecules along with accessory molecules such as CD8, intercellular adhesion molecule -1 (ICAM-1), ICAM-2, ICAM-3, leukocyte functional antigen-1 (LFA-1) (Altmann et al., *Nature* 338:521, 1989), the B7/BB1 molecule (Freeman et al., *J. Immunol.* 143:2714, 1989), LFA-3 (Singer, *Science* 255:1671, 1992; Rao, *Crit. Rev. Immunol.* 10:495, 1991), or other cell adhesion molecules. Antigenic peptide presentation in association with MHC class I molecules leads to CTL activation. Transfer and stable integration of specific sequences capable of expressing products expected to inhibit MHC antigen presentation block activation of T-cells, such as $CD8^+$ CTL, and therefore suppress graft rejection. A standard CTL assay is used to detect this response (see U.S. Ser. No. 08/116,827 now abandoned). Components of the antigen presentation pathway include the 45 Kd MHC class I heavy chain, $\beta_2$-microglobulin, processing enzymes such as proteases, accessory molecules, chaperones, and transporter proteins such as PSF1.

Thus, vectors may be generated which direct the expression of a protein or active portion of a protein capable of inhibiting MHC class I antigen presentation. An "active portion" of a protein is that fragment of the protein required for biological activity. Such fragments or active domains can be readily identified by systematically removing nucleotide sequences from the protein sequence, transforming target cells with the resulting recombinant vector construct, and determining MHC class I presentation on the surface of cells using FACS analysis or other immunological assays, such as a CTL assay.

Such vectors may direct the expression of a protein or active portion of a protein that binds to newly synthesized MHC class I molecules intracellularly, blocking transport of these molecules to the cell surface and prevents cell recognition and lysis by CTL. For instance, a 19 kD transmembrane glycoprotein, E3/19K, transcribed from the E3 region of the adenovirus 2 genome, may be expressed from a recombinant vector delivered by a gene transfer system such as described herein. Within the context of the present invention, the E3/19K protein inhibits the surface expression of MHC class I surface molecules, and cells transformed by the vector evade an immune response.

Alternatively, vectors may direct the expression of a protein or an active portion of a protein capable of binding $b_2$-microglobulin. Transport of MHC class I molecules to the cell surface for antigen presentation requires association with $b_2$-microglobulin. Thus, proteins that bind $b_2$-microglobulin and inhibit its association with MHC class I indirectly inhibit MHC class I antigen presentation. Suitable proteins include the H301 gene product from the human cytomegalovirus (Browne et al., Nature 347:770, 1990).

Graft rejection may also be suppressed by transforming tissue cells with a vector which transcribes an antisense message capable of inhibiting MHC class I antigen presentation. Briefly, oligonucleotides with nucleotide sequences complementary to the protein coding or "sense" sequence are termed "antisense". Antisense RNA molecules function as regulators of gene expression by hybridizing to complementary mRNA sequences and arresting translation (Mizuno et al., PNAS 81:1966, 1984; Heywood et al., Nucleic Acids Res. 14:6771, 1986). Antisense molecules comprising the entire sequence of the target transcript or any part thereof can be synthesized (Ferretti et al., PNAS 83:599, 1986), placed into vectors, and effectively introduced into cells to inhibit gene expression (Izant et al., Cell 36:1007, 1984).

In another aspect of the present invention, methods and compositions are provided for suppressing an immune response within an animal by transforming selected cells of the animal with a vector which transcribes a ribozyme responsible for the enzymatic cleavage of a component involved in the MHC antigen presentation. Briefly, ribozymes are RNA molecules with enzymatic cleaving activity which are used to digest other RNA molecules. They consist of short RNA molecules possessing highly conserved sequence-specific cleavage domains flanked by regions which allow accurate positioning of the enzyme relative to the potential cleavage site in the desired target molecule. They provide highly flexible tools in inhibiting the expression and activation of specific genes (Haseloff et al., Nature 334:585, 1988). Custom ribozymes can easily be designed, provided that the transcribed sequences of the targeted gene are known.

Within another aspect of the invention, multivalent vectors, i.e. those directing the expression of more than one gene of interest, such as a therapeutic protein, anti-sense RNA or ribozyme, are provided. Briefly, the efficiency of suppressing an autoimmune response, or treating another disease state, may be enhanced by transforming, transfecting, or transducing cells with a multivalent vector. Upon expression, the gene products increase the degree of interference with MHC antigen presentation by attacking a single component via two or more different routes or two different components via the same or different routes. The construction of multivalent vectors may require two or more promoters because one promoter may not ensure adequate levels of gene expression of the second and subsequent downstream genes. Alternatively, sequences such as an internal ribzome binding site (IRBS) can be placed between the various coding regions of the gene of interest to boost the level of gene expression of the second or later downstream gene(s).

The present invention provides methods and compositions suitable for inserting a sequence encoding a therapeutic protein and a sequence capable of inhibiting MHC antigen presentation in order to suppress the immune response of class I restricted cells Within an animal. A multivalent vector construct is provided which directs-the expression of a therapeutic protein of interest and a protein or active portion of the protein capable of inhibiting MHC class I antigen presentation.

Within another aspect of the present invention, a multivalent vector construct is provided which directs the expression of at least one therapeutic protein and also transcribes an antisense message or a ribozyme capable of inhibiting MHC class I antigen presentation.

Within one aspect of the present invention, methods and compositions are provided which comprises the step of administering to a warm-blooded animal, particularly a human, a vector which directs the expression of at least one immunogenic, non-tumorigenic form of an altered cellular component normally associated with tumor cells. Such methods can be performed in vivo or ex vivo. In this manner, an immune response is generated which destroys tumor cells by eleciting a potent CTL and humoral response against the altered cellular component (see U.S. Ser. No. 08/104,424 ).

The present invention is also directed towards methods and compositions for treating bacterial and viral infections, e.g., hepatitis B and C infections, as well as hepatocellular carcinomas. Immunotherapeutic approaches may be employed to induce potent class I-restricted protective and therapeutic CTL responses, as well as humoral responses. Such treatments may be accomplished by generating vector suitable for packaging into bacteriophage according to the invention, wherein the vector directs the expression of at least one immunogenic portion of a bacterial or viral (e.g., hepatitis B) antigen, such that an immune response is elicited. An "immunogenic portion" of an anitgen refers to a portion of the respective antigen which is capable, under the appropriate conditions, of causing an immune response (i.e., cell-mediated or humoral). "Portions" may be of variable size, but are preferably at least 9 amino acids long, and may include the entire antigen. Representative assays which may be utilized to determine immunogenicity (e.g., cell-mediated immune response). Cell mediated immune responses may be mediated through Major Histocompatability Complex (MHC) class I presentation, MHC Class II presentation, or both.

Mutagenesis of gpJ gene to encode receptor-specific ligands In another embodiment, receptor specific ligands are incorporated into different regions of a bacteriophage tail fiber protein such as the gpJ protein. In the gpJ protein, the carboxyl region is important in binding to lamB. Three amino acids critical for lambda infection, located at amino acid positions 1040, 1077 and 1127, have been identified (Werts, et al., *J. Bacteriol.* 176:941–947, 1994). Various receptor specific ligands may be incorporated at these sites or at other hydrophilic regions in the carboxyl tail to interact with receptors on eukaryotic cell membranes.

A number of hydrophilic regions have been identified in the gpJ protein. The most hydrophilic regions are located near amino acids 650, 770, and 900. Simple ligands may be inserted into these regions in order to target specific receptors. The resulting mutant tail fiber proteins are tested for functional activity of the inserted ligand, i.e., receptor binding, as well as for self-assembly of the tail fiber and phage particles incorporating it.

Formulation Of Bacteriophage Particles

Another aspect of the invention relates to pharmaceutical compositions comprising the bacteriophage particles described above, in combination with a pharmaceutically acceptable carrier or diluent. Such particles can be formulated in crude or, preferably, purified form. Such pharmaceutical compositions may be prepared either as a liquid solution, or as a solid form (e.g., lyophilized or dehydrated) which is resuspended in a solution prior to administration. In addition, the composition may be prepared with suitable carriers or diluents for topical administration, injection, or nasal, oral, sub-lingual, inhalant, intraocular, or enteric administration.

Pharmaceutically acceptable carriers or diluents are nontoxic to recipients at the dosages and concentrations employed. Representative examples of carriers or diluents for injectable solutions include water, isotonic saline solutions, preferably buffered at a physiological pH (such as phosphate-buffered saline or Tris-buffered saline), mannitol, dextrose, glycerol, and ethanol, as well as polypeptides or proteins such as human serum albumin (HSA). The bacteriophage particles will typically represent approximately 1 μg of material and comprise less than 1/100,000 of the total material (including water).

Pharmaceutical compositions of the present invention may also additionally include factors which stimulate cell division, and hence, uptake and incorporation of a recombinant retroviral vector. Additionally, such compositions may include inhibitors of complement activation, such as saccharides that compete with pre-existing human antibodies against alpha galactose epitopes, for example B-Disaccharide-R (Chembiomed), B-Disaccharide (Dextra), B-Trisaccharide (Dextra), B-Tetrasaccharide (Dextra), A-Fucosylated trisaccharide-R, 6-0-B-D-Galactopyranosyl-D-galactose, A-Fucosylated trisaccharide-R, Decay Accelarating Factor, and HRF20 [Neethling, et al. (1994), *Transplantation*, vol. 57, pp:959–963; Hayashi, et al. (1994), *Transplantation Proceedings*, vol. 26, no. 3, pp:1243–1244]. Such complement inhibitors may be especially effective when used with recombinant retroviruses that are produced in packaging cell lines derived from a species different from that of the patient to whom the composition is to be administered.

Pharmaceutical compositions of the present invention may also additionally include factors which suppress an immune response to the bacteriophage particles of the invention. In addition, pharmaceutical compositions of the present invention may be placed within containers or kits, along with packaging material which provides instructions regarding the use of such pharmaceutical compositions. Generally, such instructions will describe the reagent concentration, as well as within certain embodiments, relative amounts of excipient ingredients or diluents (e.g., water, saline or PBS) which may be necessary to reconstitute the pharmaceutical compositions.

Administration Of Compositions Comprising Bacteriophage Particles to Eukaryotes

Another advantage afforded by the gene transfer systems of the invention is that because of the efficiency of gene transfer with these systems, the quantitities of phage required to be administered to a patient may be vanishingly small, potentially being less than the amounts of protein and nucleic acid delivered by recombinant vital vectors. This will reduce the likelihood of eliciting an immune response against the phage-derived gene transfer system, thus enhancing the prospect for repeat administration. In addition, many more phage proteins are required for assembly than recombinant viral proteins in the case of recombinant viral particles and therefore any immune response elicited by a component may be diluted to a threshold below that required for immune induction.

In this aspect of the present invention, methods are provided for delivering a therapeutically effective amount of bacteriophage particles according to the invention. As used herein, a "therapeutically effective amount" of bacteriophage particles is an amount that promotes the desired effect, i.e., treatment of disease, expression of a desired amount of one or more proteins encoded by the vector delivered by the phage particles, etc. For example, a therapeutically effective amount of a bacteriophage particle carrying a vector directing the expression of factor VIII is that amount which, when administered to a patient suffering from hemophilia A, elicits production of sufficient factor VIII to produce therapeutically beneficial clotting, generally about 0.2 ng/mL (about 0.1% of "normal" levels) or more.

In some cases, bacteriophage particles according to the invention will be administered as an adjunct to other therapy, such as hormonal, radiation, and/or chemotherapeutic treatment. Factors influencing the amount of bacteriophage particles that will be administered include the condition to be treated, the vector construct (inlcuding the therapeutic gene (s)) employed, the age and general condition of the patient, etc.

In various embodiments of the invention, vectors carried in bacteriophage particles according to the invention and pharmaceutical compositions comprising them may be administered by various routes in vivo, or ex vivo, as described in greater detail below. Representative examples include transfection by various physical methods, such as lipofection (Felgner, et al., *Proc. Natl. Acad. Sci. USA*, 84:7413, 1989), direct DNA injection (Acsadi, et al., *Nature*, 352:815, 1991; microprojectile bombardment (Williams, et al., *Proc. Nat'l. Acad. Sci. USA*, 88:2726, 1991); liposomes of several types (see e.g., Wang, et al., *Proc. Nat'l. Acad. Sci. USA*, 84:7851, 1987); $CaPO_4$ (Dubensky, et al., *Proc. Nat'l. Acad. Sci. USA*, 81:7529, 1984); DNA ligand (Wu, et al., *J. Biol. Chem.*, 264:16985, 1989); or administration of nucleic acids alone (WO 90/11092).

When pharmaceutical compositions according to the invention are administered in vivo, i.e., to the cells of patient without prior removal of the cells from the patient, administration can be by one or more routes. In this context, "administration" is equivalent to "delivery." Typical routes of administration include traditional parenteral routes, such as intramuscular (I.M.), subcutaneous (S.C.), intravenous (I.V.), and interperitoneal (I.P.) injection. other suitable routes include nasal, pulmonary, and even direct administration into a particular tissue, such as the liver, bone marrow, etc. In addition, other routes may be employed, as described below.

Transdermal or topical application of a pharmaceutical composition may be used as an alternate route of administration because the skin is the most expansive and readily accessible organ of the human body. Transdermal delivery systems (TDS) are capable of delivering a bacteriophage particle through intact skin so that it reaches the systemic circulation in sufficient quantity to be therapeutically effective. TDS provide a variety of advantages, including elimination of gastrointestinal absorption problems and hepatic first pass effect, reduction of dosage and dose intervals, and improved patient compliance. The major components of TDS are a controlled release device composed of polymers, a bacteriophage particle carrying the desired vector construct, excipients, and enhancers, and a fastening system to fix the device to the skin. A number of polymers have been described and include, but are not limited to, gelatin, gum arabic, paraffin waxes, and cellulose acetate phthalate (Sogibayasi, et al., *J. Controlled Release*, 29:177, 1994). These polymers can be dermatologically formulated into aqueous, powder, or oil phases. Various combinations can produce lotions, pastes, ointments, creams, and gels, alone or together with the aid of emulsifiers.

Additionally, iontophoresis may be used to cause increased penetration of ionized substances into or through the skin by the application of an electrical field. This method has the advantage of being able to deliver the drug in a pulsatile manner (Singh, et al, *Dermatology*, 187:235, 1993).

Topical administration may also be accomplished by encapsulating bacteriophage particles in liposomes. Hyaluronic acid has been used as a bioadhesive ligand for the formation of liposomes to enhance adherence and retention to the extracellular matrix in cases of burns and wound healing (Yerushalmi, et al., *Arch. Biochem. and Biophys*, 313:267, 1994). As those in the art will appreciate, methods of liposome preparation can be tailored to control size and morphology. Liposomes can also be made to include one or more targeting elements to target a specific cell type.

Ocular administration is an alternate route to achieve delivery of compositions described herein. Systemic absorption occurs through contact with the conjunctival and nasal mucosae, the latter occurring as the result of drainage through the nasolacrimal duct. Formulations such as those described above which further comprise inert ingredients such as buffers, chelating agents, antioxidants, and preservatives can be incorporated into ophthalmic dosage forms intended for multiple dose use. Formulations also may consist of aqueous suspensions, ointments, gels, inserts, bioadhesives, microparticles, and nanoparticles.

The nasal cavity also offers an alternative route of administration for compositions comprising a bacteriophage particle according to the invention. For instance, the human nasal cavities have a total surface area of approximately 150 $cm^2$ and are covered by a highly vascular mucosal layer. A respiratory epithelium, comprised of columnar cells, goblet cells, and ciliary cuboidal cells, lines most of the nasal cavity (Chien, et al, *Crit. Rev. in Therap. Drug Car. Sys.*, 4:67, 1987). The subepithelium contains a dense vascular network and the venous blood from the nose passes directly into the systemic circulation, avoiding first-pass metabolism in the liver. Thus, delivery to the upper region of the nasal cavity may result in slower clearance and increased bioavailability of retroviral particles. The absence of cilia in this area is an important factor in the increased effectiveness of nasal sprays as compared to drops. The addition of viscosity-building agents, such as methycellulose, etc. can change the pattern of deposition and clearance of intranasal applications. Additionally, bioadhesives can be used as a means to prolong residence time in the nasal cavity. Various formulations comprising sprays, drops, and powders, with or without the addition of absorptive enhancers, have been described (see Wearlay, L, supra ).

Oral administration includes sublingual, buccal, and gastrointestinal delivery. Sublingual and buccal (cheek) delivery allow for rapid systemic absorption of gene transfer systems and avoid hepatic first-pass metabolism and degradation in the stomach and intestines. Unidirectional buccal delivery devices can be designed for oral mucosal absorption only. Additionally, these devices can prevent diffusion-limiting mucus buildup to allow for enhanced absorption. Delivery through the gastrointestinal tract allows for precise targeting for drug release. Depending on the formulation, bacteriophage particles can be specifically delivered to areas in the stomach, duodenum, jejunum, ileum, cecum, colon, or rectum. Oral formulations include tablets, capsules, aqueous suspensions, and gels. These may contain bioadhesive polymers, hydrodynamically balanced systems, gastroinflatable delivery devices, intragastric retention shapes, enteric coatings, excipients, or intestinal absorption promoters (Ritschel, W. A., *Math. Exp. Clin. Pharmacol.*, 13:313, 1991).

The human rectum has a surface area of between 200 to 400 $cm^2$ and is abundant in blood and lymphatic vessels. This offers an alternative route for administrating compositions according to the invention. Depending on the actual site of administration, it may be possible to bypass first-pass metabolism by the liver. Targeting of the systemic circulation can be achieved by delivering the vehicle to an area behind the internal rectal sphincter which allows absorption directly into the inferior vena cava, thereby bypassing the portal circulation and avoiding metabolism in the liver. The liver can be targeted by delivering the vehicle to the region of the ampulla recti, which allows absorption into the portal system (Ritschel, supra.). Interestingly, liver transplantation rectifies hemophilia A, and factor VIII mRNA is detectable in the liver and in isolated hepatocytes (Zatloukal, et al., supra).

Alternatively, pulmonary administration can be accomplished through aerosolization. As the lungs are highly vascularized, this type of administration allows systemic delivery. The three systems commonly used for aerosol production are: the nebulizer, the pressurized metered dose inhaler, and the dry powder inhaler, all of which are known in the art. Aerosol therapy is very common in obstructive bronchial diseases but can be used as well as for the treatment of systemic diseases. The surface area of the adult human lung is approximately 75 $m^2$ and requires only one puff of an aerosol to cover this entire area within seconds. Absorption occurs quickly because the walls of the alveoli in the deep lung are extremely thin. Absorption and clearance depends on a number of factors, including particle size and solubility (Wearley, L, supra ). Particles are preferably smaller than 5 µm in diameter.

The vaginal mucosa consists of stratified squamous epithelium. Gene delivery vehicles can be administered through the vaginal orifice onto the mucosa. Formulations include ointments, creams, and suppositories. Additional information regarding these and other routes of administration may be found in U.S. Ser. No. 08/366,788, filed Dec. 30, 1994.

As an alternative to in vivo adminstration of the bacteriophage particles of the invention, ex vivo adminstration can be employed. Ex vivo treatment envisions withdrawl or removal of a population of cells from a patient. Exemplary cell populations include bone marrow cells, liver cells, and blood cells from the umbilical cord of a newborn. Such cells may be be processed to purify desired cells for transduction prior to such procedures, for instance to obtain subsets of such cell populations, e.g., CD34+ bone marrow progenitor cells. Preferred methods of purification include various cell sorting techniques, such as antibody panning, FACS, and affinity chromatography using a matrix coupled to antibodies specifcially reactive to the desired cell type(s). Isolated cells are then transduced, after which they may be immediately re-introduced to the patient from which they were withdrawn. Alternatively, the cells may be expanded in culture by various techniques known to those skilled in the art prior to re-introduction.

In another embodiment of the invention, bacteriophage particles are administered in conjunction with another therapeutic compound. As those in the art will appreciate, such compounds may include, but are not limited to, other gene transfer systems designed to deliver one or more other therapeutic genes to the patient, as described in U.S. Ser. No. 08/368,210, filed Dec. 30, 1994.

The following examples are included to more fully illustrate the present invention. Additionally, these examples provide preferred embodiments of the invention and are not meant to limit the scope thereof. Standard methods for many of the procedures described in the following examples, or suitable alternative procedures, are provided in widely reorganized manuals of molecular biology, such as, for example "Molecular Cloning," Second Edition (Sambrook, et al., Cold Spring Harbor Laboratory Press, 1987) and "Current Protocols in Molecular Biology" (Ausubel, et al., eds. Greene Associates/Wiley Interscience, New York, 1990).

EXAMPLES

The following examples are included to more fully illustrate the present invention. Additionally, these examples provide preferred embodiments of the invention and are not meant to limit the scope thereof. Standard methods for many of the procedures described in the following examples, or suitable alternative procedures, are provided in widely reorganized manuals of molecular biology, such as, for example "Molecular Cloning," Second Edition (Sambrook, et al., Cold Spring Harbor Laboratory Press, 1987) and "Current Protocols in Molecular Biology" (Ausubel, et al., eds. Greene Associates/Wiley Interscience, New York, 1990).

Example 1

A Lambda Phage Targeted Gene Delivery System

This example provides methods for generating one or more lambda gpJ tail fiber protein mutants that can self-assemble into functional tail structures and then into infectious lambda particles which can specifically interact with a eukaryotic receptor on a cell membrane and deliver into the cell a genome packaged in the phage.

A. Isolation of gpJ Gene Sequences From Lambda

As a first step in generating lambda tail fiber mutants as described above, part or all of the gene coding for gpJ is isolated. In one approach, a 3591 bp fragment encoding a small portion of the I gene and the entire gpJ fiber protein gene which lacks the carboxy-terminal 22 amino-acids is isolated from lambda gt11 [Sambrook, et al., supra] by PCR amplification. Amplification of the desired region employs the following two synthetic oligonucleotides to prime DNA synthesis:

Forward primer:
(Sequence ID No.:2)

5'-GAACTCCCCGTATACAGACAACGG-3'

Reverse primer:
(Sequence ID No.:3)

5'-CAAAACGTATACGGCGGAATATCTG-3'

The underlined portions in these two primer sequences indicate Acc I restriction sites present in the lambda genome which provide convenient cloning sites for the isolation and reinsertion of mutant gpJ sequences into various vector constructs. Because of the paucity of Acc I sites in the lambda genome, mutant gpJ sequences can be cloned as Acc I fragments into lambda to replace the the corresponding wild type Acc I fragment.

In preparation for mutagenesis, the amplified, purified, and cut with Acc I, 3.6 kb gpJ gene fragment is cloned into an appropriate plasmid vector. The Bluescript SK+ plasmid (Stratagene, La Jolla, Calif.) is particularly useful because the gpJ gene fragment can be readily cloned into the plasmid's unique Acc I site.

In an alternative approach, the entire gpJ gene is isolated by partial a Acc I digestion of lambda gt10 [Sambrook, et al., supra] to generate a 4,213 bp fragment. This fragment is cloned into a suitable plasmid, e.g., Bluescript SK+. The functional integrity of resultant gpJ clones is tested using a complementation assay (described below) or by rapid assays using antibodies directed against the gpJ protein.

B. Complementation Assay for Testing gpJ Mutant Function

Complementation assays may be utilized as a standard test to assess the function, in terms of plaque formation, of proteins when mutagenizing gpJ genes according to this invention. A typical complementation assay involves stable transformation of a gpJ deletion mutant of lambda into E. coli. The gpJ deletion mutant is prepared by deleting an internal fragment of the gpJ gene from lambda gt11 using standard techniques (Maniatis-et al., 1989). The gpJ deletion mutant is transformed into E. coli and tested for inability to form plaques on a lawn of E. coli. Subsequent gpJ mutants are assayed for functional activity by testing their ability to complement the gpJ deleted lambda mutant to produce plaque forming phage. Functional gpJ genes give rise to plaques when transformed into E. coli, whereas non-functional mutants do not generate plaques due to their inability to promote production of phage capable of infecting neighboring cells.

C. Mutagenesis of the gpJ Gene

Mutagenic PCR is performed on cloned gpJ genes or fragments thereof by substituting manganese for magnesium in the PCR reaction buffer [Vogel and Das (1994), Molecular Microbiology 12: 811–817]. The primers described above for the isolation of gpJ sequences are used to perform mutagenic PCR. This mutagenesis procedure results in 70–80% of the amplified products containing one or more mutations. The products of the mutagenic PCR reaction are then subjected to a second round of amplification using the same primers; however, standard reaction conditions (i.e., containing magnesium) are used. The products of this reaction represent an amplified pool of gpJ gene mutations. The pool of gpJ mutants is digested with Acc I to facilitate cloning into the lambda test vector, infra.

D. Construction Of the Lambda Test Vector

In order to screen for gpJ mutants that enable a lambda phage containing a desired mutant to specifically interact with and deliver a nucleic acid molecule into a eukaryotic cell, a suitable lambda "test" vector is required. While many such lambda test vectors may be produced, the key features of any such vector are the lack of a functional gpJ gene and the presence of an indicator of expression in eukaryotic cells. It is also beneficial if the gpJ gene(s) from vectors found to encode a desired tail fiber mutant can be easily recloned from eukaryotic cells found to be transduced by the vector.

To construct such a lambda test vector, the wild type J gene is deleted from a lambda gt11 vector. One way in which this may be accomplished is to isolate the left and right fragment "arms" of lambda after partial Acc I digestion. The fragment "arms" chosen are those that, when combined, result in the deletion of the J gene Acc I fragment. Mutant J genes are then cloned into the Acc I of this lambda vector.

The indicator of expression in eukaryotic cells may be any indicator or marker gene. Representative examples of such genes are β-galactosidase, an immunogenic molecule for which a specific antibody is available (i.e., for FACS or immunofluorescence analysis, e.g., CD4, CD8, MHC class I molecules, etc.), or a gene conferring a selective growth advantage on cells containing the gene. For example, the gene encoding neomycin aminoglycoside 3'-phosphotransferase ($neo^R$) can be used. A $neo^R$ expression cassette is isolated from the plasmid vector N2 IIIBenv [Chada, et al., 1993] as a 1.8 kb Cla I fragment. This expression cassette contains a neomycin resistance gene which retains prokaryotic promoter sequences to confer kanamycin resistance when grown in bacteria, as well as an SV40 promoter for expression in eukaryotic cells. The 1.8 kb Cla I fragment is cloned into the Cla I site of Bluescript SK+to generate SK-neo. A polyadenylation signal is provided at a restriction site downstream of the $neo^R$ insertion site by incorporating bovine growth hormone transcription termination sequences from the plasmid pCDNA3 (Invitrogen, San Diego, Calif.) into a downstream site. The nucleic acid molecule comprising the SV40 promoter sequences, the $neo^R$ gene and bovine GH 3' sequences is restricted and inserted into the unique Eco R1 site of lambda gt11 using appropriate linkers. cells containing this eukaryotic nucleic acid molecule are selected using G418 as described by Chada et al., supra. In brief, HT1080 cells are selected for neomycin resistance by plating the cells in media containing G418 at a concentration of 800 µg/ml. The selective media is changed every four days for two weeks.

In an alternative approach, the gene for *E. coli* xanthine-guanine phosphoribosyl transferase (gpt), which confers resistance to mycophenolic in mammalian cells, may be used. Here, the 2.25 kb Bam H1 fragment from pMSG (Pharmacia, Milwaukee, Ill.) contains the gpt gene linked to SV40 promoter and polyadenylation signals. This fragment is cloned into the unique Eco R1 site of lambda gt11 using appropriate linkers. As those in the art will appreciate, the expression cassette may contain other selectable markers, such as genes coding for resistance to compounds such as hygromycin, phleomycin, histidinol, and methotrexate.

E. Packaging of Mutated Lambda Vectors

Because many lambda test vectors containing the mutated gpJ genes will fail to produce phage capable of infecting *E. coli*, such nucleic acid molecules may be packaged into infectious phage particles using an in vitro packaging extract. The resultant particles are used infect *E. coli* for one round of phage production. Only those vectors coding for gpJ proteins which can be assembled into intact phage particles, i.e., those comprising a lambda genome coding for the the particular gpJ gene packaged into a lambda capsid attached to a tail structure. Although many, and perhaps most, of phage particles produced from the infected bacterial cells are no longer capable of infecting other *E. coli* cells, some include altered tail fiber proteins encoded by the mutated genomes. The supernatant of this single infectious round thus contains amplified populations of each mutated phage.

In one method, In one method, gpJ mutants are amplified by PCR and ligated to lambda test vector from which the gpJ gene has been deleted and which contains the SV40 promoter driving the $neo^R$ gene for selection in eukaryotic cells. The ligation mixture is packaged in vitro using a wild type gpJ-containing tail mixture (Stratagene) and the resultant functional, i.e., infectious, phage obtained are used to infect *E. coli* for one round of phage amplification, performed according to well known techniques [see Sambrook, et al., supra].

After incubating the cells exposed to the packaged lambda test vectors for several hours at 37° C. in liquid medium, the cells are treated with chloroform to ensure efficient lysis and phage particle release. The phage population in the supernatant is then purified.

This supernatant contains a mixture of phage, some of which contain elements which enable positive selection in eukaryotic cells, i.e., phage with tail fiber proteins that allow them to interact with and deliver a vector construct encoding a selectable marker as well as the mutant tail fiber gene. To eliminate phage incorporating unmutated tail fiber proteins, the purified supernatant may be exposed to a purified preparation of Shigella lamB protein, as phage with unaltered tail fibers spontaneously eject their DNA in the presence o Shigella lamB protein.

Infection of Mammalian Cells with Packaged Vector

Phage having mutated tail fibers are then plated on eukaryotic cells, such as HT1080 fibroblasts, under selective pressure. As described above, a preferred selectable marker is resistance to the antibiotic G418, which is conferred by incorporation of a $neo^R$ gene into the vector packaged in the phage. Culture in selective media results in the survival of G418 resistant cells. Cells which survive contain a lambda vector encoding the mutant gpJ protein. Dilution cloning of these cells allows for the isolation and characterization of the mutant gpJ gene(s) which confer the desired phenotype, i.e., specific interaction with and transfer of a nucleic acid molecule into the cell, followed by expression of the gene of interest therein. Isolation is performed by PCR amplification of gpJ genes through the use of gpJ specific primers from DNA purified from the cells. The gpJ gene(s) so isolated are then characterized by such techniques as restriction mapping and DNA sequence analysis.

As an alternative to growth in selective media, lambda test vectors coding for a marker detectable in viable cells, e.g., β-galactosidase or CD4, may be used to FACS sort cells expressing the gene of interest. Because FACS sorting is extremely sensitive, $10^{14}$ bacteriophage particles may be combined with up to $10^6$ eukaryotic cells, which are then cultured for a short period to allow expression of genes introduced by the vectors. FACS selection allows those cells that take up and express the reporter gene to be rapidly identified. The mutant gpJ genes present in the selected cells are then isolated and characterized.

Because the approaches described above are based on the positive selection of one or more mutant gpJ proteins that confers specific interaction with and delivery of a nucleic acid molecule to a eukaryotic cell from a complex mixture phage harboring mutagenized gpJ vectors, amplification reactions on pools of mutagenized gpJ vectors can be performed to increase the effectiveness of the screening procedure. Upon identification of pools that contain positively selected cells, each pool is again selected for the presence of the selectable marker, i.e., resistance to an antobiotic such as G418 or expression of a reporter gene. Those pools are then further subdivided to identify the specific gpJ mutant(s) responsible for conferring the selected phenotype. Individual positive clones containing the selected mutant gpJ protein are recovered and the gpJ gene recovered by PCR.

In one method, the steps required to isolate individual eukaryotic clones is foregone by performing PCR amplification from DNA obtained from tells that have been expanded under selective pressure after being exposed to a mixture of phage containing lambda test vectors.

After identifying a mutant lambda tail fiber protein that specifically intereacts with eukaryotic cells, the corresponding mutant gpJ gene are cloned into a phage packaging cell line that produces the phage tail proteins required for phage packaging. Extracts of the tail proteins are prepared therefrom and are used to generate phage in vitro which contain one or more genes of interest. The resultant phage, capable of specifically interacting with and delivering nucleic acid molecules to eukaryotic cells, for instance may be formulated and used to introduce a nucleic acid molecule coding for a therapeutic protein, e.g., factor VIII and/or HSVTK, into a patient.

G. Control Reagents

Initially, conditions for bacteriophage infection of eukaryotic cells are determined by producing a eukaryotic control cell line which expresses the lamB protein from Shigella. A suitable eukaryotic cell may be prepared in HT1080 cells by cloning the Shigella lamB-encoding gene into an appropriate eukaryotic expression vector which targets the gene product to the cell membrane. This expression vector is then by transfected into HT1080 cells. Localization of the lamB gene product to the cell membrane is confirmed by FACS analysis after exposing the transfected cells to a fluorescently labeled antibody specifically reactive against extracellualr lamB epitopes. Cells correctly expressing the protein are designated HT-lamB.

This cell line is used as a positive control for bacteriophage infection because wild type phage such as lambda bind to the lamB protein.

In addition, efficiency of bacteriophage transduction of eukaryotic cells can be assayed using a lambda test vector encoding a SV40-neo cassette and/or a CMV-β-galactosidase construct packaged using wild type head and tail extracts. The bacteriophage may be titered on *E. coli* and HT-lamB in parallel to determine infectivity and efficiency of gene transfer. These control reagents can also be used to test the role of other lambda genes involved in infection. As described above, mutants in the lambda gpH and gpV genes have extended bacterial host ranges. Incorporation of proteins produced from mutated forms of these proteins may enhance bacteriophage-mediated gene transfer of eukaryotic cells.

H. Tissue Specific Targetting of Recombinant Vectors

Pools or clones of phage containing mutated gpJ proteins, as decsribed above, can also be used to screen a variety of different eukaryotic cell and tissue types to select phage that target a specific tisssue or cell. Phage encoding mutant gpJ proteins are applied to cultured cells derived from a variety of eukaryotic cells, particularly those from human tissues such as skin, liver, kidney, brain, blood, muscle, bone, etc. The cells are screened for infectibility and gene expression by the eukaryotic cell-infecting phage. gpJ genes found encode tail fiber proteins which target one or more eukaryotic cell types, if not previously characterized, are isolated from the transduced cells by PCR amplification as described above. These genes can then be used to produce packaging extracts which incorporate vector constructs into infectious phage particles that target those specific cell types. As those in the art will appreciate, such phage particles can also be used to identify the specific cell surface moieity with which it interacts, such as by cross-linking labeled lambda phage to cell surface receptors.

While the present invention has been described above both generally and in terms of preferred embodiments, it is understood that variations and modifications will occur to thise skilled in the art in the light of the description above. Therefore, it is intended that the appended claims cover all such variations and modifications coming within the scope of the invention as claimed.

Additionally, the publications and other materials cited herein to illuminate the background of the invenbtion, and in particular cases to provide additional details concerning its practice, are hereby incorporated by reference.

We claim:

1. A bacteriophage lambda particle comprising bacteriophage lambda structural proteins and a nucleic acid molecule comprising a nucleotide sequence exogenous to bacteriophage lambda wherein said bacteriophage structural proteins comprise a modified gpJ tail fiber protein which can bind to the membrane of an animal cell thereby causing said bacteriophage particle to bind said animal cell, and wherein said nucleic acid molecule is taken into said animal cell.

2. The bacteriophage lambda particle according to claim 1 wherein the exogenous nucleotide sequence codes for a compound selected from the group consisting of a polypeptide, an anti-sense RNA, and a ribozyme.

3. A method of producing the bacteriophage lambda particle of claim 1 comprising a) obtaining a head extract comprising said nucleic acid molecule comprising a nucleotide sequence exogenous to bacteriophage lambda in a prohead;

b) obtaining a tail extract comprising said modified lambda gpJ bacteriophage tail fiber polypeptide and;

c) combining in vitro the head extract and the tail extract to form said bacteriophage lambda particle.

4. The method of claim 3, wherein said exogenous nucleotide sequence codes for a for a compound selected from the group consisting of a polypeptide, an anti-sense RNA, and a ribozyme.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Glu  Asp  Pro  Gly  Phe  Phe  Asn  Val  Glu
    1                    5

( 2 ) INFORMATION FOR SEQ ID NO:2:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:2:

GAACTCCCCG TATACAGACA ACGG  24

( 2 ) INFORMATION FOR SEQ ID NO:3:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

CAAAACGTAT ACGGCGGAAT ATCTG  25